(12) United States Patent
Dop

(10) Patent No.: US 9,023,335 B2
(45) Date of Patent: May 5, 2015

(54) COSMETIC METHOD USING A COMPOSITION COMPRISING A SILOXANE RESIN AND A VOLATILE HYDROCARBON-BASED SOLVENT

(75) Inventor: Florence Dop, Villiers le Bacle (FR)

(73) Assignee: L'Oreal, Paris (FR)

( * ) Notice: Subject to any disclaimer, the term of this patent is extended or adjusted under 35 U.S.C. 154(b) by 586 days.

(21) Appl. No.: 12/746,454

(22) PCT Filed: Dec. 5, 2008

(86) PCT No.: PCT/FR2008/052236
§ 371 (c)(1),
(2), (4) Date: Jun. 4, 2010

(87) PCT Pub. No.: WO2009/080966
PCT Pub. Date: Jul. 2, 2009

(65) Prior Publication Data
US 2010/0260701 A1    Oct. 14, 2010

Related U.S. Application Data

(60) Provisional application No. 60/992,357, filed on Dec. 5, 2007.

(51) Int. Cl.
| | | |
|---|---|---|
| *A61K 31/74* | (2006.01) | |
| *A61K 8/02* | (2006.01) | |
| *A61K 8/58* | (2006.01) | |
| *A61Q 1/10* | (2006.01) | |
| *A61K 8/891* | (2006.01) | |
| *A61Q 1/02* | (2006.01) | |
| *A61Q 1/06* | (2006.01) | |

(52) U.S. Cl.
CPC . *A61Q 1/10* (2013.01); *A61K 8/891* (2013.01); *A61Q 1/02* (2013.01); *A61Q 1/06* (2013.01)

(58) Field of Classification Search
None
See application file for complete search history.

(56) References Cited

U.S. PATENT DOCUMENTS

| | | | | |
|---|---|---|---|---|
| 6,074,654 | A * | 6/2000 | Drechsler et al. | 424/401 |
| 6,641,805 | B1 * | 11/2003 | Morita et al. | 424/78.03 |
| 6,991,782 | B2 * | 1/2006 | Kanji et al. | 424/70.7 |
| 2006/0242773 | A1 * | 11/2006 | Kravtchenko et al. | 8/405 |
| 2006/0292096 | A1 | 12/2006 | Yu | |

FOREIGN PATENT DOCUMENTS

| | | |
|---|---|---|
| WO | 2005 075542 | 8/2005 |
| WO | 2005 075567 | 8/2005 |
| WO | 2009 071662 | 6/2009 |

OTHER PUBLICATIONS

U.S. Appl. No. 12/746,428, filed Jun. 4, 2010, Dop.
Caprasse, Virginie et al., "A new silicone resin for personal care applications", Research Disclosure, vol. 486, No. 8, pp. 1-15, XP007134333, ISSN: 0374-4353, (Oct. 1, 2004).
Kowandy, Veronique et al., "Bodied MQ-T Prophyl Silicone Resins in Color Cosmetic Applications", ip.com Journal, pp. 1-15, XP013127272, ISSN:1533-0001, (Dec. 4, 2008).

* cited by examiner

*Primary Examiner* — Blessing M Fubara
*Assistant Examiner* — Jennifer A Berrios
(74) *Attorney, Agent, or Firm* — Oblon, McClelland, Maier & Neustadt, L.L.P.

(57) ABSTRACT

The invention relates to a cosmetic method for making up and/or caring for keratinous substances, in particular the skin, comprising the application, to said keratinous substances, of a cosmetic composition comprising a siloxane resin and a volatile hydrocarbon solvent. The invention relates in particular to compositions for caring for or making up said keratinous substances.

14 Claims, No Drawings

COSMETIC METHOD USING A COMPOSITION COMPRISING A SILOXANE RESIN AND A VOLATILE HYDROCARBON-BASED SOLVENT

CROSS-REFERENCE TO RELATED APPLICATIONS

This application is a National Stage of PCT/FR08/052236 filed Dec. 5, 2008 and claims benefit of U.S. 60/992,357 filed Dec. 5, 2007.

The invention relates to a cosmetic method for making up and/or caring for keratinous substances, in particular the skin, comprising the application to said keratinous substances of a cosmetic composition comprising a siloxane resin and a volatile hydrocarbon solvent. The invention relates in particular to compositions for caring for or making up said keratinous substances.

A makeup product is used to contribute color to the skin, to mattify and to homogenize the complexion. The consumer also expects the result of the makeup to be stable over time and in particular over the course of the day.

It is known to a person skilled in the art to use several formulation routes in order to obtain a makeup result which is stable over time. The formulator can thus introduce sebum-absorbing fillers, silicone resins or also volatile silicone solvents, such as cyclopentasiloxane. The use of these starting materials can be accompanied by discomfort of the makeup (in particular characterized by feelings of tightness of the skin), either immediately after application of the product or during the day.

It thus appears necessary to provide a technical solution which makes it possible to obtain a makeup result which is stable over time, in particular over the course of the day, while retaining comfortable use, both during application and after making up, in particular during the day.

It has been found, unexpectedly, that it is possible, by combining siloxane resins with volatile solvents, more particularly volatile $C_8$ to $C_{16}$ hydrocarbon solvents, to obtain a product which is comfortable to apply and which confers a makeup result which is stable over time.

This aim and others are achieved by the present invention which describes in particular a cosmetic method for making up and/or caring for keratinous substances, in particular the skin, comprising the application, to said keratinous substances, of a composition comprising, in a physiologically acceptable medium:

i) at least one siloxane resin comprising the units:
  (i) $(R^1{}_3SiO_{1/2})_a$
  (ii) $(R^2{}_2SiO_{2/2})_b$
  (iii) $(R^3SiO_{3/2})_c$ and
  (iv) $(SiO_{4/2})_d$
with
  $R^1$, $R^2$ and $R^3$ independently representing an alkyl group having from 1 to 8 carbon atoms, an aryl group, a carbinol group or an amino group,
  a being between 0.05 and 0.5,
  b being between zero and 0.3,
  c being greater than zero,
  d being between 0.05 and 0.6,
  $a+b+c+d=1$,
provided that more than 40 mol % of the $R^3$ groups of the siloxane resin are propyl groups, and
ii) at least one volatile $C_8$ to $C_{16}$ hydrocarbon solvent.

The method according to the invention makes it possible to advantageously obtain deposited layers having a good persistence of the color throughout the day, while retaining a good level of mattness. The combination according to the invention has turned out to exhibit very good properties of persistence of the color while retaining a matt deposited layer comfortable for complexion applications, which is a particularly noteworthy result.

The composition which can be used according to the invention can be provided in various forms, in particular in the form of powders (loose or compact), of an anhydrous dispersion, of a water/oil, water/wax, oil/water, multiple (such as a water/oil/water or oil/water/oil) or wax/water emulsion or in the form of a gel. Preferably, the composition according to the invention is provided in the form of powders (loose or compact), of an anhydrous dispersion or of an inverse emulsion (i.e., water/oil emulsion).

The composition according to the invention is intended in particular for making up and/or caring for the skin.

Siloxane Resins

The siloxane resins which can be used according to the invention can be obtained by a process comprising the reaction of:

A) an MQ resin comprising at least 80 mol % of $(R^1{}_3SiO_{1/2})_a$ and $(SiO_{4/2})_d$ units,
  $R^1$ representing an alkyl group having from 1 to 8 carbon atoms, an aryl group, a carbinol group or an amino group,
  a and d being greater than zero,
  the ratio a/d being between 0.5 and 1.5;
and of
B) a propyl T resin comprising at least 80 mol % of $(R^3SiO_{3/2})_c$ units,
  $R^3$ representing an alkyl group having from 1 to 8 carbon atoms, an aryl group, a carbinol group or an amino group,
  c being greater than zero,
  provided that at least 40 mol % of the $R^3$ groups are propyl groups,
where the A/B ratio by weight is between 95:5 and 15:85.

Preferably, the A/B ratio is less than or equal to 70:30. Advantageously, the A/B ratio is equal to 30:70 or 50:50.

The resins which can be used according to the invention are in particular those described in application WO 2005/075542.

The MQ-propyl T resin according to the invention comprises units:
(R$^1{}_3$SiO$_{1/2}$)$_a$
(ii) (R$^2{}_2$SiO$_{2/2}$)$_b$
(iii) (R$^3$SiO$_{3/2}$)$_c$ and
(iv) (SiO$_{4/2}$)$_d$
which are known from the prior art and which respectively correspond to the M, D, T and Q units.

The amount of each unit present in the MQ-propyl T resin can be expressed as a molar fraction (i.e. a, b, c or d) of the total number of moles of all the M, D, T and Q units present in the MQ-propyl T resin.

The value of a (molar fraction of M units) is between 0.05 and 0.5, or alternatively between 0.15 and 0.4.

The value of b (molar fraction of D units) is between 0 and 0.3, or alternatively between 0 and 0.1, or alternatively between 0 and 0.05. Thus, the MQ-propyl T resin according to the invention can be devoid of D units or alternatively can comprise up to 0.3 molar fraction of D units.

Preferably, the MQ-propyl T resin according to the invention is devoid of D units.

The value of c (molar fraction of T units) is greater than 0, or alternatively between 0.05 and 0.65, or alternatively between 0.4 and 0.65.

The value of d (molar fraction of Q units) is between 0.05 and 0.6, or alternatively between 0.2 and 0.6, or alternatively between 0.2 and 0.55.

The MQ-propyl T resin according to the invention is characterized in that at least 40 mol %, preferably at least 50 mol %, preferably at least 90 mol % of $R_3$ alkyl groups of the T units are propyl groups.

The $R^1$, $R^2$ and $R^3$ radicals of the units of the MQ-propyl T resin independently represent an alkyl group having from 1 to 8 carbon atoms, an aryl group, a carbinol group or an amino group.

The alkyl groups can in particular be chosen from the methyl, ethyl, propyl, butyl, pentyl, hexyl and octyl groups. Preferably, the alkyl group is a methyl group or a propyl group.

The aryl groups can be chosen from the phenyl, naphthyl, benzyl, tolyl, xylyl, xenyl, methylphenyl, 2-phenylethyl, 2-phenyl-2-methylethyl, chlorophenyl, bromophenyl and fluorophenyl groups, the aryl group preferably being a phenyl group.

In the present invention, "carbinol group" is understood to mean any group comprising at least one hydroxy radical bonded to a carbon (COH). The carbinol groups can thus comprise more than one COH radical, such as, for example:

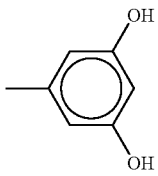

If the carbinol group is devoid of aryl groups, it comprises at least 3 carbon atoms. If the carbinol group comprises at least one aryl group, it comprises at least 6 carbon atoms.

Mention may be made, as examples of carbinol group devoid of aryl groups comprising at least 3 carbon atoms, of the groups of formula $R^4OH$ in which $R^4$ represents a divalent hydrocarbon radical comprising at least 3 carbon atoms or a divalent hydrocarbonoxy radical comprising at least 3 carbon atoms. Mention may be made, as examples of $R^4$ group, of alkylene radicals, such as —$(CH_2)_x$—, the value of x being between 3 and 10, —$CH_2CH(CH_3)$—, —$CH_2CH(CH_3)CH_2$—, —$CH_2CH_2CH(CH_2CH_3)CH_2CH_2CH_2$— and —$OCH(CH_3)(CH_2)_x$—, the value of x being between 1 and 10.

Mention may be made, as examples of carbinol group comprising aryl groups exhibiting at least 6 carbon atoms, of the groups of formula $R^5OH$ in which $R^5$ represents an arylene radical such as —$(CH_2)_xC_6H_4$—, x having a value of between 0 and 10, —$CH_2CH(CH_3)(CH_2)_xC_6H_4$—, x having a value of between 0 and 10, —$(CH_2)_xC_6H_4(CH_2)_x$—, x having a value of between 1 and 10. The carbinol groups comprising aryl groups generally comprise from 6 to 14 atoms.

Amino group according to the invention is understood to mean in particular groups of formula —$R^6NH_2$ or —$R^6NHR^7NH_2$, $R^6$ representing a divalent hydrocarbon radical having at least 2 carbon atoms and $R^7$ representing a divalent hydrocarbon radical having at least 2 carbon atoms. The $R^6$ group generally represents an alkylene radical having from 2 to 20 carbon atoms. Mention may be made, as examples of $R^6$ group, of the ethylene, propylene, —$CH_2CHCH_3$—, butylene, —$CH_2CH(CH_3)CH_2$—, pentamethylene, hexamethylene, 3-ethylhexamethylene, octamethylene and decamethylene groups.

The $R^7$ group generally represents an alkylene radical having 2 to 20 carbon atoms. Mention may be made, as examples of $R^7$ group, of the ethylene, propylene, —$CH_2CHCH_3$—, butylene, —$CH_2CH(CH_3)CH_2$—, pentamethylene, hexamethylene, 3-ethylhexamethylene, octamethylene and decamethylene groups.

The amino groups are generally —$CH_2CH_2CH_2NH_2$, —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$ and —$CH_2CH_2NHCH_2CH_2NHC_4H_9$.

Preferably, $R^1$ represents a methyl group, $R^2$ represents a methyl group or a phenyl group and $R^3$ represents a propyl group.

Preferably, the MQ-propyl T resin according to the invention is devoid of D units, and $R^1$ represents a methyl group, and $R^3$ represents a propyl group.

The D, T or Q siloxane units of the MQ-propyl T resin according to the invention can comprise hydroxy (—OH) groups and/or alkoxy groups. Such siloxane units comprising hydroxy and/or alkoxy groups are commonly present in siloxane resins having the general formula $R_nSiO_{(4-n)/2}$.

These hydroxy groups typically result from the reaction of a hydrolyzable group on the siloxane unit with water; the alkoxy groups result from an incomplete hydrolysis when alkoxysilane precursors are used or result from the exchange of alcohol with hydrolyzable groups.

Preferably, the total amount by weight of —OH groups present in the MQ-propyl T resin is approximately 3%, preferably 2%, preferably 1.5%. Preferably, the total amount by weight of alkoxy groups present in the MQ-propyl T resin is less than or equal to 20% by weight, preferably less than or equal to 10% by weight.

Preferably, the siloxane resin present in said composition comprises the units:
(i) $(R^1_3SiO_{1/2})_a$
(iii) $(R^3SiO_{3/2})_c$ and
(iv) $(SiO_{4/2})_d$
with
  $R^1$ and $R^3$ independently representing an alkyl group having from 1 to 8 carbon atoms; preferably, $R^1$ is a methyl group and $R^3$ is a propyl group,
  a being between 0.05 and 0.5,
  c being greater than zero,
  d being between 0.05 and 0.6,
  a+c+d=1,
provided that more than 40 mol % of the $R^3$ groups of the siloxane resin are propyl groups.

There exist no restrictions relating to the molecular weight of the MQ-propyl T siloxane resins but, generally, the number-average molecular weight ($M_N$) is between 3000 and 10 000 or between 5000 and 8000.

The MQ-propyl T resins which can be used according to the invention can be prepared according to the processes known in the state of the art for preparing siloxane resins of general formula $R_nSiO_{(4-n)/2}$, where R is an alkyl group and n is less than 1.8.

Alternatively, the MQ-propyl T resins can be prepared according to the methods described below.

The MQ-propyl T resins according to the invention are illustrated by the MQ-propyl T resins comprising the following units:
  $((CH_3)_3SiO_{1/2})_a$
  $(R^3SiO_{3/2})_c$ where $R^3$=$CH_3CH_2CH_2$—, and
  $(SiO_{4/2})_d$;

or the following units:
$((CH_3)_3SiO_{1/2})_a$
$((CH_3)_2SiO_{2/2})_b$
$(R^3SiO_{3/2})_c$ where $R^3$=$CH_3CH_2CH_2$—, and
$(SiO_{4/2})_d$;
or the following units:
$((CH_3)_3SiO_{1/2})_a$
$((CH_3)_2SiO_{2/2})_b'((CH_3)(C_6H_5)SiO_{2/2})_{b'}$
$(R^3SiO_{3/2})_c$ where $R^3$=$CH_3CH_2CH_2$—, and
$(SiO_{4/2})_d$;
or the following units:
$((CH_3)_3SiO_{1/2})_a$
$((CH_3)_2SiO_{2/2})_b$
$(R^3SiO_{3/2})_c$ where $R^3$=$CH_3CH_2CH_2$—, $(C_6H_5SiO_{3/2})_c$ and
$(SiO_{4/2})_d$;
or the following units:
$((CH_3)_3SiO_{1/2})_a$
$((CH_3)_2SiO_{2/2})_b'((CH_3)(C_6H_5)SiO_{2/2})_{b'}$
$(R^3SiO_{3/2})_c$ where $R^3$=$CH_3CH_2CH_2$—, $(C_6H_5SiO_{3/2})_c$ and
$(SiO_{4/2})_d$;
where a has a total value in the resin of between 0.05 and 0.5, the sum b+b' has a total value in the resin of between 0 and 0.3, c has a total value in the resin of between 0.05 and 0.65 and d has a total value in the resin of between 0.05 and 0.6.

The siloxane resins which can be used according to the invention can be obtained by a process comprising the reaction between:

A) an MQ resin comprising at least 80 mol % of $(R^1_3SiO_{1/2})_a$ and $(SiO_{4/2})_d$ units,
  $R^1$ representing an alkyl group having from 1 to 8 carbon atoms, an aryl group, a carbinol group or an amino group,
  a and d being greater than zero,
  the ratio a/d being between 0.5 and 1.5;
and
B) a propyl T resin comprising at least 80 mol % of $(R^3SiO_{3/2})_c$ units,
  $R^3$ representing an alkyl group having from 1 to 8 carbon atoms, an aryl group, a carbinol group or an amino group,
  c being greater than zero,
  provided that at least 40 mol % of the $R^3$ groups are propyl groups,
where the A/B ratio by weight is between 95:5 and 15:85.

The component A) is an MQ resin comprising at least 80 mol % of $(R^1_3SiO_{1/2})_a$ and $(SiO_{4/2})_d$ units, where $R^1$ is as defined above, i.e. represents an alkyl group having from 1 to 8 carbon atoms, an aryl group, a carbinol group or an amino group, a and d are greater than zero and the ratio a/d is between 0.5 and 1.5.

The MQ resins which can be used as component A) and their method of preparation are known from the prior art. For example, U.S. Pat. No. 2,814,601, belonging to Currie and al., dated Nov. 26, 1957 describes a process for manufacturing MQ resins by conversion of a water-soluble silicate into a silicic acid monomer or a silicic acid oligomer by using an acid. Once the appropriate polymerization has been carried out, trimethylchlorosilane ends are introduced in order to obtain the MQ resin. Another process of preparation of MQ resins is described in U.S. Pat. No. 2,857,356, belonging to Goodwin, dated Oct. 21, 1958. Goodwin describes a process for the manufacture of an MQ resin by cohydrolysis of a mixture of an alkyl silicate and of a trialkylsilane organopolysiloxane which can be hydrolyzed with water. The MQ resins suitable as component A) in the present invention can comprise D and T units, provided that at least 80 mol %, indeed even 90 mol %, of the total siloxane units are M and Q units. The MQ resins can also comprise hydroxy groups. The MQ resins can thus comprise hydroxy groups in a total amount by weight of between 2 and 10%, preferably between 2 and 5%. The MQ resins can also comprise additional ends, residual hydroxy groups being for this reacted with the M groups.

The component B) is a propyl T resin comprising at least 80 mol % of $(R^3SiO_{3/2})_c$ units, $R^3$ being as defined above, i.e. representing an alkyl group having from 1 to 8 carbon atoms, an aryl group, a carbinol group or an amino group, c being greater than 0, provided that at least 40 mol % of the $R^3$ groups are propyl groups. Preferably, the propyl T resin according to the invention is a silsesquioxane resin. Silsesquioxane resins are well known in the state of the art and are generally obtained by hydrolysis of an organosilane comprising three hydrolyzable groups, such as halogen or alkoxy groups, present in the molecule. The component B) can thus be obtained by hydrolysis of propyltrimethoxysilane, propyltriethoxysilane or propyltripropoxysilane or by cohydrolysis of the abovementioned propylalkoxysilanes with various alkoxysilanes. Mention may be made, as examples of these alkoxysilanes, of methyltrimethoxysilane, methyltriethoxysilane, methyltriisopropoxysilane, dimethyldimethoxysilane and phenyltrimethoxysilane. Propyltrichlorosilane can also be hydrolyzed, alone or in the presence of alcohol. In this case, the cohydrolysis can be carried out by adding methyltrichlorosilane, dimethyldichlorosilane, phenyltrichlorosilane or similar chlorosilanes and methyltrimethoxysilane, methyltriethoxysilane, methyltriisopropoxysilane or similar methylalkoxysilanes. Mention may be made, as alcohols suitable for this purpose, of methanol, ethanol, n-propyl alcohol, isopropyl alcohol, butanol, methoxyethanol, ethoxyethanol or similar alcohols. Mention may be made, as examples of solvents of hydrocarbon type which can be used, of toluene, xylene or similar aromatic hydrocarbons; hexane, heptane, isooctane or similar saturated and linear or partially branched hydrocarbons; and cyclohexane or similar aliphatic hydrocarbons.

The propyl T resins as component B) according to the invention can comprise M, D and Q units, provided that at least 80 mol %, indeed even 90 mol % of the total siloxane units are T units. The propyl T resins can also comprise hydroxy groups. Preferably, the propyl T resins comprise between 3 and 8% by weight of hydroxy groups.

A polyorganosiloxane can also be added to the process according to the invention as component C).

The polyorganosiloxanes of use as component C) according to the invention comprise $R^2_2SiO_{2/2}$ or $R^3SiO_{3/2}$ units. The polyorganosiloxane can be added in order to introduce various D and T units into the MQ-propyl T resins, in order to modify the properties of the resulting resins. The structure or the formula of the polyorganosiloxane is not limiting, provided that said polyorganosiloxane comprises a measurable amount of $R^2_2SiO_{2/2}$ or $R^3SiO_{3/2}$ units and that the total amount of polyorganosiloxane added to the reaction between A) and B) does not result in more than 50 mol % of D or T units in the reaction mixture. The polyorganosiloxane can comprise combinations of M, D, T and Q units, provided that at least the D or T units are present. Thus, the polyorganosiloxane can be chosen from silicone fluids, gums or resins known from the prior art and comprising D or T units, or their mixtures. The D units typically comprise methyl or phenyl groups or their mixtures as $R^2$ groups. The T units typically comprise methyl or phenyl groups or their mixtures as $R^3$ groups. The polyorganosiloxane can be a fluid linear polydiorganosiloxane having a viscosity of between 10 and 1000 cS (mm$^2$/s). The fluid polydiorganosiloxane can be a polydimethylsiloxane or a polymethylphenylsiloxane. The polyorganosiloxane can also be an organosilsesquioxane resin. The organosilsesquioxane resin is typically a methylsilsesquioxane resin or a phenylsilsesquioxane resin.

The components A), B) and optionally C) can react by any method known from the prior art for acting on M, D, T and Q units. However, preferably, the components A), B) and optionally C) react by a condensation reaction in the presence of a catalyst. The MQ resin is typically present in an aromatic hydrocarbon or siloxane solvent. Condensation reaction catalysts which can be used are in particular metal hydroxides, such as potassium hydroxide or sodium hydroxide; metal salts, such as silanolates, carboxylates and carbonates; amines; titanates, such as tetrabutyl titanate; and their mixtures. Typically, the reaction between the components A), B) and optionally C) is carried out by heating the reaction mixture to temperatures ranging from 50 to 140° C., preferably ranging from 100 to 140° C. The reaction can take place in a semicontinuous, continuous or batch process.

Preferably, said siloxane resin is obtained by a process comprising the reaction between:
A) an MQ resin comprising at least 80 mol % of $(R^1_3SiO_{1/2})_a$ and $(SiO_{4/2})_d$ units,
$R^1$ representing a methyl group,
a and d being greater than zero,
the ratio a/d being between 0.5 and 1.5;
and
B) a propyl T resin comprising at least 80 mol % of $(R^3SiO_{3/2})_c$ units,
$R^3$ representing a propyl group,
c being greater than zero,
where the A/B ratio by weight is between 95:5 and 15:85; preferably, the A/B ratio by weight is 30:70.

The A/B ratio by weight in the reaction is between 95:5 and 15:85, preferably between 95:5 and 20:80, preferably between 90:10 and 20:80.

Preferably, the A/B ratio by weight is equal to 85:15 or 50:50 or 30:70 or 95:5. Preferably, the A/B ratio by weight is equal to 30:70.

The amount of component C) can vary but provided that it results in a content of additional D or T units of less than 30 mol %, with respect to the total molar amount of siloxane units of the reaction mixture.

The composition according to the invention comprises an amount of siloxane resin, by weight of active material (dry matter), ranging from 0.5 to 60% by weight, with respect to the total weight of the composition, preferably from 3 to 60% by weight and better still from 4 to 60% by weight, with respect to the total weight of said composition.

According to a specific form, the amount of siloxane resin, by weight of active material (dry matter), will advantageously range from 3 to 60% by weight and better still from 6 to 60% by weight, with respect to the total weight of said composition. These contents are in particular suitable for the compositions in anhydrous form and especially for the compositions in the stick form, such as lipsticks.

According to another specific form, the amount of siloxane resin, by weight of active material (dry matter), will advantageously range from 3 to 30% by weight and better still from 4 to 20% by weight, with respect to the total weight of said composition. These contents are in particular suitable for compositions in the form of emulsions and especially for compositions in the form of W/O emulsions, such as liquid foundations.

As specified above, the amount of siloxane resin, by weight of active material (dry matter), is advantageously such that the ratio by weight of volatile $C_8$ to $C_{16}$ hydrocarbon solvent to the siloxane resin is less than 10, preferably less than or equal to 7 and better still from 0.1 to 5.

Volatile Hydrocarbon Solvent

The composition according to the invention can comprise at least one volatile solvent, in particular one volatile oil.

In the context of the present invention, the volatile solvent or oil is preferably a volatile hydrocarbon solvent or oil.

The term "hydrocarbon solvent" or "hydrocarbon oil" is understood to mean a solvent or an oil formed essentially, or even composed, of carbon and hydrogen atoms and optionally of oxygen or nitrogen atoms and not comprising a silicon or fluorine atom; it can comprise ester, ether, amine or amide groups.

The term "volatile solvent" or "volatile oil" is understood to mean a solvent or an oil (or a nonaqueous medium) capable of evaporating on contact with skin in less than one hour at ambient temperature and atmospheric pressure. The volatile oil is a volatile cosmetic oil which is liquid at ambient temperature and which has in particular a non-zero vapor pressure at ambient temperature and atmospheric pressure, especially a vapor pressure ranging from 0.13 Pa to 40 000 Pa ($10^{-3}$ to 300 mmHg), preferably ranging from 1.3 Pa to 13 000 Pa (0.01 to 100 mmHg) and preferably ranging from 1.3 Pa to 1300 Pa (0.01 to 10 mmHg).

In addition, the volatile solvent or the volatile oil generally has a boiling point, measured at atmospheric pressure, ranging from 150° C. to 260° C. and preferably ranging from 170° C. to 250° C.

The composition according to the invention can comprise a volatile hydrocarbon solvent or a volatile hydrocarbon oil chosen in particular from hydrocarbon oils having a flashpoint ranging from 40° C. to 102° C., preferably ranging from 40° C. to 55° C. and preferably ranging from 40° C. to 50° C.

Mention may be made, as volatile hydrocarbon solvent or volatile hydrocarbon oil, of volatile hydrocarbon oils having from 8 to 16 carbon atoms, in particular from 9 to 13 carbon atoms, and their mixtures, in particular branched $C_8$-$C_{16}$ alkanes, such as $C_8$-$C_{16}$ isoalkanes (also known as isoparaffins), such as, in particular, isododecane, isodecane or isohexadecane, and for example the oils sold under the Isopar or Permethyl trade names, and their mixtures. Preferably, the volatile hydrocarbon oil is chosen from $C_8$-$C_{16}$ isoalkanes, in particular isododecane, isodecane or isohexadecane, volatile linear $C_8$-$C_{16}$ alkanes, and their mixtures.

For products for making up the skin, in particular foundations and lipsticks, use will advantageously be made of volatile linear hydrocarbon solvents or oils having from 8 to 16 carbon atoms, in particular from 9 to 13 carbon atoms.

Preference is given to volatile hydrocarbon solvents having from 9 to 13 carbon atoms. Mention may in particular be made, as volatile $C_8$ to $C_{16}$ hydrocarbon solvent, of linear or branched alkanes, in particular branched alkanes, such as $C_8$-$C_{16}$ isoalkanes (also known as isoparaffins), isododecane, isodecane or isohexadecane, and for example the oils sold under the Isopar or Permethyl trade names, and their mixtures. Preferably, the volatile hydrocarbon solvent having from 8 to 16 carbon atoms is chosen from isododecane, isodecane, isohexadecane and their mixtures.

According to a specific embodiment, the volatile solvent is isododecane.

According to another specific embodiment, the volatile hydrocarbon solvent is a volatile linear alkane exhibiting a flashpoint within the range varying from 70 to 120° C. and more particularly from 80 to 100° C. and in particular a flashpoint of approximately 89° C.

A volatile linear alkane suitable for the invention is liquid at ambient temperature (approximately 25° C.).

According to one embodiment, an alkane suitable for the invention can be a volatile linear alkane comprising from 8 to 16 carbon atoms, in particular from 10 to 15 carbon atoms and more particularly from 11 to 13 carbon atoms.

A volatile linear alkane suitable for the invention can advantageously be of vegetable origin. Such an alkane can be obtained, directly or in several stages, from a vegetable starting material, such as an oil, a butter, a wax, and the like.

Mention may be made, as examples of alkanes suitable for the invention, of the alkanes described in the patent application from Cognis WO 2007/068371.

These alkanes are obtained from fatty alcohols, themselves obtained from coconut oil or palm oil.

Mention may be made, as examples of linear alkane suitable for the invention, of n-nonane (C9), n-decane (C10), n-undecane (C11), n-dodecane (C12), n-tridecane (C13), n-tetradecane (C14), n-pentadecane (C15), n-hexadecane (C16) and n-heptadecane (C17), and their mixtures, in particular the mixture of n-undecane (C11) and of n-tridecane (C13) sold under the reference of Cetiol UT by Cognis.

According to a specific embodiment, a volatile linear alkane suitable for the invention can be chosen from n-nonane, n-undecane, n-dodecane, n-tridecane, n-heptadecane and their mixtures.

More particularly, a volatile linear alkane suitable for the invention can be employed in the form of an n-undecane/n-tridecane mixture.

Preferably, in such a mixture, the n-undecane:n-tridecane ratio by weight can be from 50:50 to 90:10, preferably varying from 60:40 to 80:20, preferably varying from 65:35 to 75:25.

In particular, a composition according to the invention can comprise an n-undecane:n-tridecane mixture in a ratio by weight of 70:30. Such a mixture is sold under the name Cetiol UT by Cognis.

Another subject matter of the present invention is a composition capable of being employed in a method according to the invention comprising, in a physiologically acceptable medium, at least one siloxane resin as defined above and at least one volatile $C_8$ to $C_{16}$ hydrocarbon solvent chosen from $C_8$-$C_{16}$ isoalkanes, as defined above, volatile linear $C_8$-$C_{16}$ alkanes, as defined above, and their mixtures.

As specified above, in the composition according to the invention, the amount of volatile $C_8$ to $C_{16}$ hydrocarbon solvent by weight is advantageously such that the ratio by weight of volatile $C_8$ to $C_{16}$ hydrocarbon solvent to the siloxane resin is less than 10, preferably less than or equal to 7 and better still from 0.1 to 5, in particular when the volatile $C_8$ to $C_{16}$ hydrocarbon solvent is isododecane.

For products for making up the skin, in particular foundations, use will advantageously be made of volatile linear hydrocarbon solvents having from 9 to 13 carbon atoms.

The volatile solvent or oil can be present in the composition according to the invention in a content ranging from 0.1 to 90% by weight, with respect to the total weight of the composition, preferably ranging from 1 to 70% by weight and preferentially ranging from 5 to 50% by weight.

Thus, the subject matter of the present invention is more specifically a cosmetic method for making up and/or caring for keratinous substances, in particular the skin, comprising the application, to said keratinous substances, of a composition comprising, in a physiologically acceptable medium:

i) at least one siloxane resin comprising the units:
  (i) $(R^1_3SiO_{1/2})_a$
  (ii) $(R^2_2SiO_{2/2})_b$
  (iii) $(R^3SiO_{3/2})_c$ and
  (iv) $(SiO_{4/2})_d$
with
  $R^1$, $R^2$ and $R^3$ independently representing an alkyl group having from 1 to 8 carbon atoms, an aryl group, a carbinol group or an amino group,
  a being between 0.05 and 0.5,
  b being between zero and 0.3,
  c being greater than zero,
  d being between 0.05 and 0.6,
  a+b+c+d=1,
provided that more than 40 mol % of the $R^3$ groups of the siloxane resin are propyl groups, and
  ii) at least one volatile $C_8$-$C_{16}$ hydrocarbon solvent in a content of 1 to 70% by weight, with respect to the total weight of said composition.

According to a specific form, the volatile $C_8$-$C_{16}$ hydrocarbon solvent can be present in a content ranging from 1 to 70% by weight, in particular from 1 to 60% by weight, preferably from 2 to 20% by weight and more specifically from 3 to 15% by weight, with respect to the total weight of the composition.

Advantageously, the amount of volatile $C_8$ to $C_{16}$ hydrocarbon solvent by weight is advantageously such that the ratio by weight of volatile $C_8$ to $C_{16}$ hydrocarbon solvent to the siloxane resin is less than 10, preferably less than or equal to 7 and better still from 0.1 to 5.

The composition according to the invention can comprise one or more other components and in particular oils, pasty compounds, hard or soft waxes, rheological additives, coloring materials, in particular pigments or fillers, not surface-treated with a hydrophobic agent, polymers, in particular those comprising saccharide or carboxylate groups, or their mixtures.

Physiologically Acceptable Medium

The term "physiologically acceptable medium" is intended to denote a medium suitable in particular for the application of a composition of the invention to the skin or the lips.

The physiologically acceptable medium is generally suited to the nature of the support on which the composition has to be applied and to the appearance under which the composition has to be packaged.

The composition according to the invention can be provided in various forms, in particular in the form of powders (loose or compact), of an anhydrous composition, of a dispersion, of an emulsion, such as in particular a water/oil, water/wax, oil/water, multiple or wax/water emulsion, or else in the form of a gel.

A composition of the invention is preferably an emulsion, in particular a direct or inverse emulsion, or an anhydrous composition.

A dispersion can be produced in an aqueous phase or in an oily phase.

An emulsion can have an oily or aqueous continuous phase. Such an emulsion can, for example, be an inverse (W/O) or direct (O/W) emulsion, or a multiple (W/O/W or O/W/O) emulsion.

In the case of the emulsions, the inverse (W/O) emulsions are preferred.

An anhydrous composition is a composition comprising less than 2% by weight of water, indeed even less than 0.5% of water, and is in particular devoid of water. If appropriate, amounts of water which are as low can in particular be introduced by ingredients of the composition which may comprise residual amounts thereof.

The composition according to the invention can be provided in the form of a fluid, for example a pasty or liquid fluid. It can also be provided in the form of a loose or compact powder, of a soft paste or of a cream. For example, it can be an oil-in-water, water-in-oil or multiple emulsion, a solid emulsion, in particular of water-in-oil type, a solid or soft gel which is in particular anhydrous, in the loose or compact powder form and even in a two-phase form.

The composition under consideration according to the invention is generally provided in the form of a composition for making up and/or caring for keratinous substances, for example of a foundation, in particular to be applied to the face or the neck, of a concealer, of a complexion corrector, of a tinted cream, of a face powder, of a lipstick, of a lip balm or of a makeup composition for the body.

Aqueous Phase

The composition according to the invention can comprise at least one aqueous phase.

The aqueous phase comprises water. A water suitable for the invention can be a floral water, such as cornflower water, and/or a mineral water, such as water from Vittel, water from Lucas or water from La Roche Posay, and/or a thermal water.

The aqueous phase can also comprise water-miscible (at ambient temperature –25° C.) organic solvents, such as, for example, monoalcohols having from 2 to 6 carbon atoms, such as ethanol or isopropanol; polyols having in particular from 2 to 20 carbon atoms, preferably having from 2 to 10 carbon atoms, and preferentially having from 2 to 6 carbon atoms, such as glycerol, propylene glycol, butylene glycol, pentylene glycol, hexylene glycol, dipropylene glycol or diethylene glycol; glycol ethers (having in particular from 3 to 16 carbon atoms), such as mono-, di- or tripropylene glycol ($C_1$-$C_4$)alkyl ethers or mono-, di- or triethylene glycol ($C_1$-$C_4$)alkyl ethers, and their mixtures.

The aqueous phase can additionally comprise stabilizing agents, for example sodium chloride, magnesium dichloride and magnesium sulfate.

The aqueous phase can also comprise any water-soluble or water-dispersible compound compatible with an aqueous phase, such as gelling agents, film-forming polymers, thickeners, surfactants and their mixtures.

In particular, a composition of the invention can comprise an aqueous phase in a content varying from 1% to 80% by weight, in particular from 5% to 50% by weight and more particularly from 10% to 45% by weight, with respect to the total weight of the composition.

According to another embodiment, a composition of the invention can be anhydrous.

An anhydrous composition can comprise less than 5% by weight of water, with respect to the total weight of the composition, and in particular less than 3% by weight of water, especially less than 2% by weight of water and more particularly less than 1% by weight of water, with respect to the total weight of the composition.

More particularly, an anhydrous composition can be devoid of water.

Fatty Phase

A cosmetic composition in accordance with the present invention can comprise at least one liquid and/or solid fatty phase.

In particular, a composition of the invention can comprise at least one liquid fatty phase.

The term "oil" is understood to mean any fatty substance in the liquid form at ambient temperature (20-25° C.) and at atmospheric pressure.

A composition of the invention can comprise a liquid fatty phase in a content varying from 1 to 90% by weight, in particular from 5 to 80% by weight, in particular from 10 to 70% by weight and more particularly from 20 to 50% by weight, with respect to the total weight of the composition.

The oily phase suitable for the preparation of the cosmetic compositions according to the invention can comprise oils which may or may not be hydrocarbon, silicone or fluorinated oils, or their mixtures.

The oils can be chosen from volatile or nonvolatile oils, or their mixture. In this context, the volatile oils can be volatile oils which are different from those which have to be present in the composition according to the invention and which have already been described above. The other volatile oils can be silicone or fluorinated oils.

Within the meaning of the present invention, the term "nonvolatile oil" is understood to mean an oil having a vapor pressure of less than 0.13 Pa.

Within the meaning of the present invention, the term "silicone oil" is understood to mean an oil comprising at least one silicon atom and in particular at least one Si—O group.

The term "fluorinated oil" is understood to mean an oil comprising at least one fluorine atom. The oils can optionally comprise oxygen, nitrogen, sulfur and/or phosphorus atoms, for example in the form of hydroxy or acid radicals.

Volatile Oils

In addition to the volatile oils identified above, use may thus be made of volatile silicones, such as, for example, volatile linear or cyclic silicone oils, in particular those having a viscosity ≤8 centistokes (cSt) ($8\times10^{-6}$ $m^2/s$), and having in particular from 2 to 10 silicon atoms and especially from 2 to 7 silicon atoms, these silicones optionally comprising alkyl or alkoxy groups having from 1 to 10 carbon atoms. Mention may in particular be made, as volatile silicone oil which can be used in the invention, of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and their mixtures.

Use may also be made of volatile fluorinated oils, such as nonafluoromethoxybutane or perfluoromethylcyclopentane, and their mixtures.

According to one embodiment, a composition of the invention can comprise from 1% to 80% by weight, indeed even from 5% to 70% by weight, indeed even from 10% to 60% by weight and in particular from 15% to 50% by weight of volatile oil, with respect to the total weight of the composition.

Nonvolatile Oils

The nonvolatile oils can be chosen in particular from nonvolatile fluorinated hydrocarbon oils and/or nonvolatile silicone oils.

Mention may in particular be made, as nonvolatile hydrocarbon oil, of:

hydrocarbon oils of animal origin, such as perhydrosqualene, hydrocarbon oils of vegetable origin, such as phytosteryl esters, such as phytosteryl oleate, phytosteryl isostearate and phytosteryl/octyldodecyl lauroyl glutamate (Ajinomoto, Eldew PS203), triglycerides composed of esters of fatty acids and of glycerol, in particular, the fatty acids of which can have chain lengths varying from $C_4$ to $C_{36}$ and in particular from $C_{18}$ to $C_{36}$, it being possible for these oils to be linear or branched and saturated or unsaturated; these oils can in particular be heptanoic or octanoic triglycerides, shea oil, alfalfa oil, poppy oil, Hokkaido squash oil, millet oil, barley oil, quinoa oil, rye oil, candlenut oil, passionflower oil, shea butter, apricot oil, aloe oil, sweet almond oil, peach kernel oil, peanut oil, arara oil, argan oil, avocado oil, baobab oil, borage oil, broccoli oil, calendula oil, calophyllum oil, camelina oil, canola oil, carrot oil, safflower oil, hemp oil, rapeseed oil, cottonseed oil, coconut oil, cucumber seed oil, cereal germ oil, in particular wheat germ oil, jojoba oil, lily oil, macadamia oil, maize oil, meadowfoam oil, Saint John's wort oil, monoi oil, hazelnut oil, apricot kernel oil, walnut oil, olive oil, evening primrose oil, palm oil, blackcurrant seed oil, kiwi seed oil, grape seed oil, pistachio oil, pumpkinseed oil, musk rose oil, sesame oil, soybean oil, sunflower oil, castor oil, mink oil, turtle oil and watermelon oil, and their mixtures, or triglycerides of caprylic/capric acids, such as those sold by Stéarineries Dubois or those sold under the names Miglyol 810®, 812® and 818® by Dynamit Nobel, linear or branched hydrocarbons of mineral or synthetic origin, such as liquid paraffins and their derivatives, liquid petrolatum, polydecenes, polybutenes, hydrogenated polyisobutene, such as Parleam, or squalane, synthetic ethers having from 10 to 40 carbon atoms, synthetic esters, such as oils of formula $R_1COOR_2$, in which $R_1$ represents a residue of a linear or branched fatty acid comprising from 1 to 40 carbon atoms and $R_2$ represents a hydrocarbon chain, in particular a branched hydrocarbon chain, comprising from 1 to 40 carbon atoms, provided that $R_1+R_2$ is ≥10. The esters can be chosen in particular from fatty acid and alcohol esters, such as, for example, cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, hydroxylated esters, such as isostearyl lactate or octyl hydroxystearate, diisopropyl adipate, heptanoates, in particular isostearyl heptanoate, octanoates, decanoates or ricinoleates of alcohols or polyalcohols, such as propylene glycol dioctanoate, cetyl octanoate, tridecyl octanoate, 2-ethylhexyl palmitate and 4-diheptanoate, alkyl benzoate, polyethylene glycol diheptanoate, propylene glycol di(2-ethylhexanoate) and their mixtures, benzoates of $C_{12}$-$C_{15}$ alcohols, hexyl laurate, esters of neopentanoic acid, such as isodecyl neopentanoate, isotridecyl neopentanoate, isostearyl neopentanoate or octyldodecyl neopentanoate, esters of isononanoic acid, such as isononyl isononanoate, isotridecyl isononanoate or octyl isononanoate, or hydroxylated esters, such as isostearyl lactate or diisostearyl malate, esters of polyols and esters of pentaerythritol, such as dipentaerythritol tetrahydroxystearate/tetraisostearate, esters of dimer diols and of dimer diacids, such as Lusplan DD-DA5® and Lusplan DD-DA7®, which are sold by Nippon Fine Chemical and are described in application US 2004-175338, copolymers of dimer diol and of dimer diacid and their esters, such as dimer dilinoleyl diol/dimer dilinoleic copolymers and their esters, such as, for example, Plandool-G, copolymers of polyols and of dimer diacids, and their esters, such as Hailuscent ISDA, or the dilinoleic acid/butanediol copolymer, fatty alcohols comprising a branched and/or unsaturated carbon chain having from 12 to 26 carbon atoms which are liquid at ambient temperature, such as 2-octyldodecanol, isostearyl alcohol, oleyl alcohol, 2-hexyldecanol, 2-butyloctanol and 2-undecylpentadecanol, higher $C_{12}$-$C_{22}$ fatty acids, such as oleic acid, linoleic acid, linolenic acid and their mixtures, and dialkyl carbonates, it being possible for the 2 alkyl chains to be identical or different, such as dicaprylyl carbonate, sold under the name Cetiol CC® by Cognis, oils of high molar mass having in particular a molar mass ranging from approximately 400 to approximately 10 000 g/mol, in particular from approximately 650 to approximately 10 000 g/mol, in particular from approximately 750 to approximately 7500 g/mol and more particularly varying from approximately 1000 to approximately 5000 g/mol. Mention may in particular be made, as oil of high molar mass which can be used in the present invention, of the oils chosen from:

lipophilic polymers, esters of linear fatty acids having a total carbon number ranging from 35 to 70, hydroxylated esters, aromatic esters, esters of fatty alcohols or of fatty acids which are branched and comprise from 24 to 28 carbon atoms, silicone oils, oils of vegetable origin, and their mixtures, fluorinated oils which are optionally partially hydrocarbon-modified and/or silicone-modified, such as fluorosilicone oils, fluorinated polyethers or fluorosilicones, such as described in the document EP-A-847 752;

silicone oils, such as polydimethylsiloxanes (PDMS), which are nonvolatile and linear or cyclic; polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethylsiloxy) diphenylsiloxanes, diphenyl dimethicones, diphenyl(methyldiphenyl)trisiloxanes or (2-phenylethyl) trimethylsiloxysilicates, and their mixtures.

Polymer:

The compositions according to the invention can comprise an additional polymer which may or may not be film-forming.

In the present invention, the term "film-forming polymer" is understood to mean a polymer capable of forming, by itself alone or in the presence of an additional agent which is able to form a film, a film which is macroscopically continuous and which adheres to keratinous substances, and preferably a cohesive film, and better still a film having a cohesion and mechanical properties such that said film can be isolable and handleable in isolation, for example when said film is produced by casting on a nonstick surface, such as a Teflon- or silicone-treated surface.

The composition comprises at least one aqueous phase and the additional polymer can be present in this aqueous phase. In this case, the additional polymer will preferably be a polymer in dispersion or an amphiphilic or associative polymer.

The term "polymer in dispersion" is understood to mean water-insoluble polymers present in the form of particles of variable size. The polymer may or may not be crosslinked. The mean particle size is typically between 25 and 500 nm, preferably between 50 and 200 nm. The following polymers in aqueous dispersion can be used: Ultrasol 2075 from Ganz Chemical, Daitosol 5000AD from Daito Kasei, Avalure UR 450 from Noveon, DynamX from National Starch, Syntran 5760 from Interpolymer, Acusol OP 301 from Röhm & Haas or Neocryl A 1090 from Avecia.

The acrylic dispersions sold under the names Neocryl XK-9012, Neocryl A-1070®, Neocryl A-1090®, Neocryl BT-62®, Neocryl A-1079® and Neocryl A-523® by Avecia-Neoresins, Dow Latex 432® by Dow Chemical, Daitosol 5000 AD® or Daitosol 5000 SJ® by Daito Kasey Kogyo; Syntran 5760® by Interpolymer, Soltex OPT by Röhm & Haas, the aqueous dispersions of acrylic or styrene/acrylic polymers sold under the trade name Joncryl® by Johnson Polymer or also the aqueous polyurethane dispersions sold under the names Neorez R-981® and Neorez R-974® by Avecia-Neoresins, the names Avalure UR-405®, Avalure UR-410®, Avalure UR-425®, Avalure UR-450®, Sancure 875®, Sancure 861®, Sancure 878® and Sancure 2060® by Goodrich, Impranil 85® by Bayer or Aquamere H-1511® by Hydromer; the sulfopolyesters sold under the trade name Eastman AQ® by Eastman Chemical Products, or vinylic dispersions, such as Mexomer PAM® from Chimex, and their mixtures, are other examples of aqueous dispersions of particles of film-forming polymers which are dispersible in water.

The term "amphiphilic or associative polymers" is understood to mean polymers comprising one or more hydrophilic parts which render them partially soluble in water and one or more hydrophobic parts via which the polymers form an association or interact. The following associative polymers can be used: Nuvis FX1100 from Elementis, Aculyn 22, Aculyn 44, Aculyn 46 from Röhm & Haas or Viscophobe DB1000 from Amerchol. Diblock copolymers composed of a hydrophilic block (polyacrylate, polyethylene glycol) and of a hydrophobic block (polystyrene, polysiloxane) can also be used.

Polymers soluble in an aqueous phase comprising monodisperse particles shall be avoided as they can bring about aggregation of the monodisperse particles. The film-forming polymer can thus be insoluble in such an aqueous phase.

The composition comprises at least one oily phase and the film-forming polymer can be present in this oily phase. The polymer can then be in dispersion or in solution. Polymers of NAD (nonaqueous dispersion) type or microgels (for example KSGs) can be used, and also polymers of the silicone-modified polyamide type or styrene-based copolymers (Kraton, Regalite).

Mention may be made, as examples of nonaqueous dispersions of fat-dispersible film-forming polymer in the form of nonaqueous dispersions of polymer particles in one or more silicone and/or hydrocarbon oils, which particles can be stabilized at their surface by at least one stabilizing agent, in particular a block, grafted or random polymer, of acrylic dispersions in isododecane, such as Mexomer PAP® from Chimex, or dispersions of particles of a grafted ethylenic polymer, preferably an acrylic polymer, in a liquid fatty phase, the ethylenic polymer advantageously being dispersed in the absence of additional stabilizer at the surface of the particles, such as described in particular in the document WO 04/055081.

Mention may be made, among film-forming polymers which can be used in the composition of the present invention, of synthetic polymers of radical type or of polycondensate type, polymers of natural origin, and their blends.

The term "radical film-forming polymer" is understood to mean a polymer obtained by polymerization of monomers possessing unsaturation, in particular ethylenic unsaturation, each monomer being capable of homopolymerizing.

The film-forming polymers of radical type can in particular be vinyl polymers or copolymers, in particular acrylic polymers.

The film-forming vinyl polymers can result from the polymerization of monomers possessing ethylenic unsaturation having at least one acid group and/or of the esters of these acidic monomers and/or of the amides of these acidic monomers.

Use may be made, as monomer carrying an acid group, of unsaturated α,β-ethylenic carboxylic acids, such as acrylic acid, methacrylic acid, crotonic acid, maleic acid or itaconic acid. Use is preferably made of (meth)acrylic acid and crotonic acid and more preferentially of (meth)acrylic acid.

The esters of acidic monomers are advantageously chosen from esters of (meth)acrylic acid (also known as (meth)acrylates), in particular alkyl (meth)acrylates, especially $C_1$-$C_{30}$ alkyl (meth)acrylates, preferably $C_1$-$C_{20}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth)acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

Esters of (meth)acrylic acid which are particularly preferred are alkyl (meth)acrylates. According to the present invention, the alkyl group of the esters can be either fluorinated or perfluorinated, that is to say that a portion or all of the hydrogen atoms of the alkyl group are substituted by fluorine atoms.

Mention may be made, as amides of the acidic monomers, for example, of (meth)acrylamides, in particular N-alkyl (meth)acrylamides, especially N—($C_2$-$C_{12}$ alkyl)(meth)acrylamides. Mention may be made, among N-alkyl(meth)acrylamides, of N-ethylacrylamide, N-(t-butyl)acrylamide, N-(t-octyl)acrylamide and N-undecylacrylamide.

The film-forming vinyl polymers can also result from the homopolymerization or from the copolymerization of monomers chosen from vinyl esters and styrene monomers. In particular, these monomers can be polymerized with acidic monomers and/or their esters and/or their amides, such as those mentioned above.

Mention may be made, as examples of vinyl esters, of vinyl acetate, vinyl neodecanoate, vinyl pivalate, vinyl benzoate and vinyl t-butylbenzoate.

Mention may be made, as styrene monomers, of styrene and α-methylstyrene.

Mention may be made, among film-forming polycondensates, of polyurethanes, polyesters, polyesteramides, polyamides, epoxy ester resins or polyureas.

The polyurethanes can be chosen from anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and their blends.

The polyesters can be obtained in a known way by polycondensation of dicarboxylic acids with polyols, in particular diols.

The dicarboxylic acid can be aliphatic, alicyclic or aromatic. Mention may be made, as examples of such acids, of: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers can be used alone or as a combination of at least two dicarboxylic acid monomers. The choice is preferably made, among these monomers, of phthalic acid, isophthalic acid or terephthalic acid.

The diol can be chosen from aliphatic, alicyclic or aromatic diols. Use is preferably made of a diol chosen from: ethylene glycol, diethylene glycol, triethylene glycol, 1,3-propanediol, cyclohexanedimethanol or 1,4-butanediol. Use may be made, as other polyols, of glycerol, pentaerythritol, sorbitol or trimethylolpropane.

Polyesteramides can be obtained analogously to the polyesters by polycondensation of diacids with diamines or amino alcohols. Use may be made, as diamines, of ethylenediamine, hexamethylenediamine, meta-phenylenediamine or para-phenylenediamine. Use may be made, as amino alcohol, of monoethanolamine.

The polyester can additionally comprise at least one monomer carrying at least one —$SO_3M$ group, with M representing a hydrogen atom, an ammonium ion $NH_4^+$ or a metal ion, such as, for example, an $Na^+$, $Li^+$, $K^+$, $Mg^{2+}$, $Ca^{2+}$, $Cu^{2+}$, $Fe^{2+}$ or $Fe^{3+}$ ion. Use may in particular be made of a bifunctional aromatic monomer comprising such an —$SO_3M$ group.

The aromatic ring system of the bifunctional aromatic monomer additionally carrying an —$SO_3M$ group as described above can be chosen, for example, from the benzene, naphthalene, anthracene, biphenyl, oxydiphenyl, sulfonyldiphenyl or methylenediphenyl ring systems. Mention may be made, as example of bifunctional aromatic monomer additionally carrying an —$SO_3M$ group, of: sulfoisophthalic acid, sulfoterephthalic acid, sulfophthalic acid or 4-sulfonaphthalene-2,7-dicarboxylic acid.

By way of example, the film-forming polymer can be a polymer dissolved in a liquid fatty phase comprising oils or organic solvents (the film-forming polymer is then described as a fat-soluble polymer). Preferably, the liquid fatty phase comprises a volatile oil, optionally as a mixture with a non volatile oil.

Mention may be made, as examples of fat-soluble polymer, of copolymers of vinyl ester (the vinyl group being directly connected to the oxygen atom of the ester group and the vinyl ester having a saturated, linear or branched, hydrocarbon radical of 1 to 19 carbon atoms bonded to the carbonyl of the ester group) and of at least one other monomer which can be a vinyl ester (other than the vinyl ester already present), an α-olefin (having from 8 to 28 carbon atoms), an alkyl vinyl ether (the alkyl group of which comprises from 2 to 18 carbon atoms) or an ally or methallyl ester (having a saturated, linear or branched, hydrocarbon radical of 1 to 19 carbon atoms bonded to the carbonyl of the ester group).

These copolymers can be crosslinked using crosslinking agents which can be either of the vinyl type or of the allyl or methallyl type, such as tetraallyloxyethane, divinylbenzene, divinyl octanedioate, divinyl dodecanedioate and divinyl octadecanedioate.

Mention may be made, as examples of these copolymers, of the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene, crosslinked with 0.2% of divinylbenzene, and allyl propionate/allyl stearate, crosslinked with 0.2% of divinylbenzene.

Mention may be made, as example of fat-soluble film-forming polymers, of copolymers of a vinyl ester and of at least one other monomer which can be a vinyl ester, in particular vinyl neodecanoate, vinyl benzoate and vinyl t-butylbenzoate, an α-olefin, an alkyl vinyl ether or an allyl or methallyl ester.

Mention may also be made, as fat-soluble film-forming polymers, of fat-soluble copolymers and in particular those resulting from the copolymerization of vinyl esters having from 9 to 22 carbon atoms or of alkyl acrylates or methacrylates, the alkyl radicals having from 10 to 20 carbon atoms.

Such fat-soluble copolymers can be chosen from copolymers of poly(vinyl stearate), of poly(vinyl stearate) crosslinked using divinylbenzene, diallyl ether or diallyl phthalate, copolymers of poly(stearyl (meth)acrylate), of poly(vinyl laurate), of poly(lauryl (meth)acrylate), it being possible for these poly(meth)acrylates to be crosslinked using ethylene glycol dimethacrylate or tetraethylene glycol dimethacrylate.

The fat-soluble copolymers defined above are known and are described in particular in application FR-A-2 232 303; they can have a weight-average molecular weight ranging from 2000 to 500 000 and preferably from 4000 to 200 000.

Mention may also be made, as fat-soluble film-forming polymers which can be used in the invention, of polyalkylenes and in particular copolymers of $C_2$-$C_{20}$ alkenes, such as polybutene, alkylcelluloses with a saturated or unsaturated and linear or branched $C_1$ to $C_8$ alkyl radical, such as ethylcellulose and propylcellulose, copolymers of vinylpyrrolidone (VP) and in particular copolymers of vinylpyrrolidone and of $C_2$ to $C_{40}$ alkene and better still $C_3$ to $C_{20}$ alkene. Mention may be made, as examples of VP copolymer which can be used in the invention, of the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

Mention may also be made of silicone resins, generally soluble or swellable in silicone oils, which are crosslinked polyorganosiloxane polymers. The nomenclature of silicone resins is known under the name of "MDTQ", the resin being described according to the various siloxane monomer units which it comprises, each of the letters "MDTQ" characterizing one type of unit.

Mention may be made, as examples of commercially available polymethylsilsesquioxane resins, of those which are sold by Wacker under the reference Resin MK, such as Belsil PMS MK, or by Shin-Etsu under the reference KR-220L.

Mention may be made, as examples of commercially available polypropylsilsesquioxane resins, of those which are sold under the reference DC670 by Dow Corning.

Mention may be made, as siloxysilicate resins, of trimethylsiloxysilicate (TMS) resins, such as those sold under the reference SR1000 by General Electric or under the reference TMS 803 by Wacker. Mention may also be made of trimethylsiloxysilicate resins sold in a solvent, such as cyclomethicone, sold under the names KF-7312J by Shin-Etsu or "DC 749" or "DC 593" by Dow Corning.

Mention may also be made of copolymers of silicone resins, such as those mentioned above with polydimethylsiloxanes, for example the pressure-sensitive adhesive copolymers sold by Dow Corning under the reference BIO-PSA and described in the document U.S. Pat. No. 5,162,410 or the silicone copolymers resulting from the reaction of a silicone resin, such as those described above, and of a diorganosiloxane, such as are described in the document WO 2004/073626.

By way of example, the film-forming polymer can be a film-forming linear ethylenic block polymer which preferably comprises at least one first block and at least one second block having different glass transition temperatures (Tg), said first and second blocks being connected to one another via an intermediate block comprising at least one constituent monomer of the first block and at least one constituent monomer of the second block.

Advantageously, the first and second blocks of the block polymer are incompatible with one another.

Such polymers are described, for example, in the documents EP 1 411 069 and WO 04/028488.

The film-forming polymer can be chosen from polymers and/or block or random copolymers comprising in particular polyurethanes, polyacrylics, silicones, fluoropolymers, butyl rubbers, ethylene copolymers, natural gums and polyvinyl alcohols and their blends. The monomers of the block or random copolymers comprising at least one combination of monomers, the polymer of which results in a glass transition temperature below ambient temperature (25° C.), can be chosen in particular from butadiene, ethylene, propylene, acrylic, methacrylic, isoprene, isobutene, a silicone and their mixtures.

The film-forming polymer can also be present in the composition in the form of particles in dispersion in an aqueous phase or in a nonaqueous solvent phase, generally known under the name of latex or pseudolatex. The techniques for the preparation of these dispersions are well known to a person skilled in the art.

The composition according to the invention can comprise a plasticizing agent which promotes the formation of a film with the film-forming polymer. Such a plasticizing agent can be chosen from all the compounds known to a person skilled in the art as being capable of performing the desired role.

Mention may be made, as other examples of a film-forming system which can be used in the compositions according to the invention, of the systems in which the film is formed in situ during the application of the composition or of a mixture of compositions comprising two silicone compounds which react when they are brought into contact with one another. Such systems are described in particular in application WO 2007/071706, the content of which is incorporated here by way of reference. Systems of this type are also described in applications US 2007/142575 or US 2007/142599, the contents of which are also incorporated here by way of reference.

Other Polymers:

The compositions according to the invention can comprise an elastomer, in particular a polyglycerolated silicone elastomer. Use is made, by way of example, of a crosslinked organopolysiloxane elastomer which can be obtained by a crosslinking addition reaction of a diorganopolysiloxane comprising at least one hydrogen bonded to the silicon and of polyglycerolated compounds having groups possessing ethylenic unsaturation, in particular in the presence of a platinum catalyst.

Use may be made, as polyglycerolated silicone elastomers, of those sold under the names "KSG-710", "KSG-810", "KSG-820", "KSG-830" and "KSG-840" by Shin-Etsu.

The compositions according to the invention can in addition comprise an additional emulsifying silicone elastomer.

Use is made, by way of examples, of polyoxyalkylenated elastomers, such as described in particular in U.S. Pat. No. 5,236,986, U.S. Pat. No. 5,412,004, U.S. Pat. No. 5,837,793 and U.S. Pat. No. 5,811,487, the contents of which are incorporated by way of reference.

Use may be made, as polyoxyalkylenated silicone elastomer, of those sold under the names "KSG-21", "KSG-20", "KSG-30", "KSG-31", KSG-32", "KSG-33", "KSG-210", "KSG-310", "KSG-320", "KSG-330", "KSG-340" and "X-226146" by Shin-Etsu and "DC9010" and "DC9011" by Dow Corning.

The compositions according to the invention can additionally comprise a nonemulsifying elastomer.

Nonemulsifying elastomers are described in particular in applications JP-A-61-194009, EP-A-242 219, EP-A-285 886 and EP-A-765 656, the contents of which are incorporated by way of reference.

Use may be made, as spherical nonemulsifying elastomers, of those sold under the names "DC9040", "DC9041", "DC9509", "DC9505" and "DC 9506" by Dow Corning.

The spherical nonemulsifying silicone elastomer can also be provided in the form of a crosslinked organopolysiloxane elastomer powder coated with silicone resin, in particular with silsesquioxane resin, as described, for example, in U.S. Pat. No. 5,538,793, the content of which is incorporated by way of reference. Such elastomers are sold under the names "KSP-100", "KSP-101", "KSP-102", "KSP-103", "KSP-104" and "KSP-105" by Shin-Etsu.

Other crosslinked organopolysiloxane elastomers in the form of spherical powders can be powders formed of hybrid silicone functionalized by fluoroalkyl groups, sold in particular under the name "KSP-200" by Shin-Etsu; or powders formed of hybrid silicone functionalized by phenyl groups, sold in particular under the name "KSP-300" by Shin-Etsu.

Use may also be made, in the compositions according to the invention, of silicone elastomers with an MQ group, such as those sold by Wacker under the names Belsil RG100, Belsil RPG33 and, preferably, Belsil RG80.

Structuring Agents:

The composition according to the invention can comprise a structuring agent.

The term "structuring agent" is understood to mean a compound capable of increasing the viscosity of the composition. The structuring agent makes it possible in particular to obtain a composition which can exhibit a texture ranging from fluid textures to solid textures.

The structuring agent can be present in the composition in a content ranging from 0.05% to 40% by weight, with respect to the total weight of the composition, preferably ranging from 0.1% to 30% by weight and preferentially ranging from 0.1% to 25% by weight.

The structuring agent can be chosen in particular from thickeners (thickeners for an oily medium; thickeners for an aqueous medium), organic gelling agents, waxes, pasty compounds or gums.

The thickening agent for an aqueous medium can be chosen from:
hydrophilic clays,
hydrophilic pyrogenic silica,
water-soluble cellulose thickeners, guar, xanthan, locust bean, scleroglucan, gellan, rhamsan, karaya or carrageenan gums, alginates, maltodextrins, starch and its derivatives, or hyaluronic acid and its salts, the poly(glyceryl (meth)acrylate) polymers sold under the names of "Hispagel" or "Lubragel" by Hispano Quimica or Guardian, polyvinylpyrrolidone, polyvinyl alcohol, crosslinked polymers and copolymers of acrylamide, such as those sold under the names of "PAS 5161" or "Bozepol C" by Hoechst, of "Sepigel 305" by SEPPIC by Allied Colloids, the crosslinked methacryloyloxyethyltrimethylammonium chloride homopolymers sold under the name of "Salcare SC95" by Allied Colloids, or associative polymers and in particular associative polyurethanes.

Such thickening agents are described in particular in application EP-A-1 400 234, the content of which is incorporated by way of reference.

The thickening agent for an oily medium can be chosen from:

silicone carboxylates, silicone saccharides, organophilic clays, hydrophobic pyrogenic silicas, alkylated guar gums (with $C_1$-$C_6$ alkyl group), such as those described in EP-A-708 114;

hydrophobic celluloses, gelling polymers for an oil, such as triblock or star polymers resulting from the polymerization or copolymerization of at least one monomer comprising an ethylene group, such as the polymers sold under the name Kraton;

polymers with a weight-average molecular weight of less than 100 000, comprising a) a polymer backbone having hydrocarbon repeat units which are provided with at least one heteroatom and optionally b) at least one optionally functionalized pendant fatty chain and/or at least one optionally functionalized end fatty chain, having from 6 to 120 carbon atoms, which are bonded to these hydrocarbon units, such as described in applications WO-A-02/056847 and WO-A-02/47619, the contents of which are incorporated by way of reference; especially, polyamide resins (in particular comprising alkyl groups having from 12 to 22 carbon atoms), such as those described in U.S. Pat. No. 5,783,657, the content of which is incorporated by way of reference;

silicone-modified polyamide resins, such as described in application EP-A-1 266 647 and in the French patent application filed under No. 02/16039, the content of which is incorporated by way of reference.

Such thickening agents are described in particular in application EP-A-1 400 234, the content of which is incorporated by way of reference.

The organic gelling agents can be chosen from those described in application WO-A-03/105788, the content of which is incorporated by way of reference.

Mention may in particular be made, by way of examples, of:

bisurea derivatives of general formula (I):

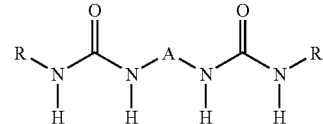

in which:

A is a group of formula:

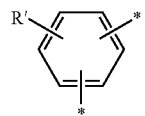

with R' being a linear or branched $C_1$ to $C_4$ alkyl radical and the * symbolizing the points of attachment of the group A to each of the two nitrogen atoms of the remainder of the compound of general formula (I), and R is a saturated or unsaturated noncyclic monobranched $C_6$ to $C_{15}$ alkyl radical, the hydrocarbon chain of which is optionally interrupted by 1 to 3 heteroatoms chosen from O, S and N, or one of their salts or isomers described in particular in patent application FR-A-2 892 303, silicone-modified bisurea derivatives of general formula (I) or one of their salts and/or isomers:

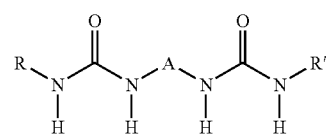

in which:

A is a group of formula (II):

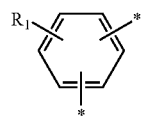

with $R_1$ being a linear or branched $C_1$ to $C_4$ alkyl radical and the * symbolizing the points of attachment of the group A to each of the two nitrogen atoms of the remainder of the compound of general formula (I), and R and R', which are identical or different, are chosen from:
i) radicals of formula (III):

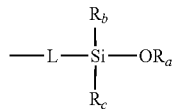
(III)

in which:
L is a simple bond or a saturated or unsaturated, linear, branched and/or cyclic, divalent carbon, in particular hydrocarbon (alkylene), radical which comprises from 1 to 18 carbon atoms and which can comprise from 1 to 4 heteroatoms chosen from N, O and S;
$R_a$ is:
a) a saturated or unsaturated, linear, branched and/or cyclic, carbon, in particular hydrocarbon (alkyl), radical which comprises from 1 to 18 carbon atoms and which can comprise from 1 to 8 heteroatoms chosen from N, O, Si and S; or else
b) a silicone radical of formula:

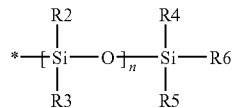

with n being between 0 and 100, in particular between 1 and 80, indeed even from 2 to 20;
and R2 to R6 being, independently of one another, linear or branched carbon, in particular hydrocarbon (alkyl), radicals which have from 1 to 12, in particular from 1 to 6, carbon atoms and which can comprise from 1 to 4 heteroatoms, in particular O;
$R_b$ and $R_c$, are chosen, independently of one another, from:
a) saturated or unsaturated, linear, branched and/or cyclic, carbon, in particular hydrocarbon (alkyl), radicals which comprise from 1 to 18 carbon atoms and which can comprise from 1 to 4 heteroatoms chosen from N, O, Si and S;
b) radicals of formula:

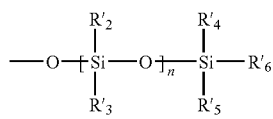

with n being between 0 and 100, in particular between 1 and 80, indeed even from 2 to 20;
and $R'_2$ to $R'_6$ being, independently of one another, linear or branched carbon, in particular hydrocarbon (alkyl), radicals which have from 1 to 12, in particular from 1 to 6, carbon atoms and which can comprise from 1 to 4 heteroatoms, in particular O,
and
ii) saturated or unsaturated, linear, branched and/or cyclic, $C_1$ to $C_{30}$ alkyl radicals optionally comprising from 1 to 3 heteroatoms chosen from O, S, F and N; it being understood that at least one of the R and/or R' radicals is of formula (III), such as those described in patent application FR-A-2 900 819,
the bisurea derivatives described in patent application FR-A-2 894 476.

The structuring agents can be composed of waxes. The term "wax" is understood to mean, within the meaning of the present invention, a lipophilic compound which is solid at ambient temperature (25° C.), which exhibits a reversible solid/liquid change in state and which has a melting point of greater than or equal to 30° C. which can range up to 120° C.

On bringing the wax to the liquid state (melting), it is possible to render it miscible with the oils which may be present and to form a microscopically homogeneous mixture but, on bringing the temperature of the mixture back to ambient temperature, recrystallization of the wax in the oils of the mixture is obtained. The melting point of the wax can be measured using a differential scanning calorimeter (DSC), for example the calorimeter sold under the name DSC 30 by Mettler.

The wax can also exhibit a hardness ranging from 0.05 MPa to 15 MPa and preferably ranging from 6 MPa to 15 MPa. The hardness is determined by the measurement of the compressive force measured at 20° C. using the texture analyzer sold under the name TA-TX2i by Rheo, equipped with a stainless steel cylinder with a diameter of 2 mm which is displaced at the measuring rate of 0.1 mm/s and which penetrates the wax to a penetration depth of 0.3 mm.

The waxes can be hydrocarbon, fluorinated and/or silicone waxes and can be of vegetable, mineral, animal and/or synthetic origin. In particular, the waxes exhibit a melting point of greater than 30° C. and better still of greater than 45° C.

Mention may be made, as wax which can be used in the composition of the invention, of beeswax, carnauba wax, candelilla wax, paraffin wax, microcrystalline waxes, rice bran wax, olive waxes (photowax olive 14L48, photowax olive 18L57), ceresin or ozokerite; synthetic waxes, such as polyethylene waxes or Fischer-Tropsch waxes, or silicone waxes, such as alkyl or alkoxy dimethicones having from 16 to 45 carbon atoms.

By way of indication, the composition can comprise from 0.1 to 50% by weight of waxes, with respect to the total weight of the composition, and better still from 1 to 30% by weight.

The gums are generally high molecular weight polydimethylsiloxanes (PDMSs) or cellulose gums or polysaccharides and the pasty substances are generally hydrocarbon compounds, such as lanolins and their derivatives, or alternatively PDMSs.

Surfactants

The composition according to the invention can comprise at least one surfactant.

The surfactant can be lipophilic and/or hydrophilic, and used alone or as a blend.

The surfactant can be chosen from nonionic, anionic, cationic or amphoteric surfactants.

The nonionic surfactant can be chosen from:
a $C_8$-$C_{22}$ alkyl dimethicone copolyol, that is to say an oxypropylenated and/or oxyethylenated polymethyl [($C_8$-$C_{22}$)alkyl](dimethyl)(methyl)siloxane.

The $C_8$-$C_{22}$ alkyl dimethicone copolyol is advantageously a compound of following formula (I):

$$(CH_3)_3Si-O{\left[\begin{array}{c}CH_3\\|\\Si-O\\|\\(CH_2)_p\\|\\CH_3\end{array}\right]}_o {\left[\begin{array}{c}CH_3\\|\\Si-O\\|\\(CH_2)_q\\|\\O\\|\\PE\end{array}\right]}_m {\left[\begin{array}{c}CH_3\\|\\Si-O\\|\\CH_3\end{array}\right]}_n Si(CH_3)_3 \quad (I)$$

in which:
  PE represents $-(C_2H_4O)_x-(C_3H_6O)_y-R$, R being chosen from a hydrogen atom and an alkyl radical of 1 to 4 carbon atoms, x ranging from 0 to 100 and y ranging from 0 to 80, x and y not simultaneously being 0,
  m ranging from 1 to 40,
  n ranging from 10 to 200,
  o ranging from 1 to 100,
  p ranging from 7 to 21,
  q ranging from 0 to 4,
and, preferably:
R=H
m=1 to 10,
n=10 to 100,
o=1 to 30,
p=15
q=3.

Mention may be made, as $C_8$-$C_{22}$ alkyl dimethicone copolyol, of cetyl dimethicone copolyol, such as the product sold under the name Abil EM-90 by Goldschmidt.

a dimethicone copolyol, that is to say an oxypropylenated and/or oxyethylenated polydimethyl(methyl)siloxane. It does not comprise a long-chain alkyl group of more than 8 carbon atoms, in particular a $C_8$-$C_{22}$ alkyl group.

Use may be made, as dimethicone copolyol, of those corresponding to the following formula (II):

$$R_1-\underset{\underset{CH_3}{|}}{\overset{\overset{CH_3}{|}}{Si}}O{\left[\underset{\underset{CH_3}{|}}{\overset{\overset{CH_3}{|}}{SiO}}\right]}_A{\left[\underset{\underset{R_2}{|}}{\overset{\overset{CH_3}{|}}{SiO}}\right]}_B\underset{\underset{CH_3}{|}}{\overset{\overset{CH_3}{|}}{Si}}-R_3 \quad (II)$$

in which:
$R_1$, $R_2$ and $R_3$ represent, independently of one another, a $C_1$-$C_6$ alkyl radical or a $-(CH_2)$, $-(OCH_2CH_2)_y-(OCH_2CH_2)_z-OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; provided that A and B are not simultaneously equal to zero;
x is an integer ranging from 1 to 6;
y is an integer ranging from 1 to 30;
z is an integer ranging from 0 to 5.

According to a preferred embodiment of the invention, in the compound of formula (II), $R_1=R_3=$methyl radical, x is an integer ranging from 2 to 6 and y is an integer ranging from 4 to 30. $R_4$ is in particular a hydrogen.

Mention may be made, as example of compounds of formula (II), of the compounds of formula (III):

$$(CH_3)_3SiO-[(CH_3)_2SiO]_A-(CH_3SiO)_B-\underset{\underset{(CH_2)_2-(OCH_2CH_2)_y-OH}{|}}{Si(CH_3)_3} \quad (III)$$

in which A is an integer ranging from 20 to 105, B is an integer ranging from 2 to 10 and y is an integer ranging from 10 to 20.

Mention may also be made, as example of silicone compounds of formula (II), of the compounds of formula (IV):

$$HO-(CH_2CH_2O)_y-(CH_2)_3-[(CH_3)_2SiO]_{A'}-[(CH_3)_2Si]-(CH_2)_3-(OCH_2CH_2)_y-OH \quad (IV)$$

in which A' and y are integers ranging from 10 to 20.

Use may be made, as dimethicone copolyol, of those sold under the names DC 5329, DC 7439-146, DC2-5695 and Q4-3667 by Dow Corning and KF-6013, KF-6015, KF-6016 and KF-6017 by Shin-Etsu.

The compounds DC 5329, DC 7439-146 and DC2-5695 are compounds of formula (III) where, respectively, A is 22, B is 2 and y is 12, A is 103, B is 10 and y is 12, and A is 27, B is 3 and y is 12.

Mention may also be made, as nonionic surfactant, of polyol fatty acid esters, such as sorbitol mono-, di-, tri- or sesqui-oleates or -stearates, glycerol mono-, di-, tri- or sesqui-oleates or -stearates, or glycerol or polyethylene glycol laurates; polyethylene glycol fatty acid esters (polyethylene glycol monostearate or monolaurate); polyoxyethylenated sorbitol fatty acid esters (stearate, oleate); or polyoxyethylenated alkyl (lauryl, cetyl, stearyl, octyl)ethers.

Mention may be made, as anionic surfactant, of carboxylates (sodium 2-(2-hydroxyalkyloxy)acetate), amino acid derivatives (N-acylglutamates, N-acylglycinates, acylsarcosinates), alkyl sulfates, alkyl ether sulfates and their oxyethylenated derivatives, sulfonates, isethionates and N-acyl-isethionates, taurates and N-acyl-N-methyltaurates, sulfosuccinates, alkyl sulfoacetates, phosphates and alkyl phosphates, polypeptides, alkyl polyglycoside anionic derivatives (acyl-D-galactoside uronate), soaps of fatty acids, and their mixtures.

Use may be made, as amphoteric and zwitterionic surfactant, of betaines, N-alkyl amido betaines and their derivatives, glycine derivatives, sultaines, alkyl polyaminocarboxylates, alkyl amphoacetates, and their mixtures.

Such surfactants are described in particular in application WO-A-02/056854, the content of which is incorporated by way of reference.

The surfactant can be present in the composition according to the invention in a content ranging from 0.1% to 10% by weight, with respect to the total weight of the composition, preferably ranging from 0.5% to 8% by weight and preferentially ranging from 0.5% to 7% by weight.

Coloring Materials:

The composition according to the invention can comprise at least one coloring material. The coloring material can be chosen from pulverulent coloring materials (in particular pigments and pearlescent agents) or water-soluble or fat-soluble coloring materials.

The term "pigments" should be understood as meaning white or colored and inorganic or organic particles of any shape which are insoluble in the physiological medium and which are intended to color the composition.

The term "pearlescent agents" should be understood as meaning iridescent particles of any shape produced in particular by certain shellfish in their shells or else synthesized.

The pigments can be white or colored and inorganic and/or organic. Mention may be made, among inorganic pigments, of titanium dioxide, optionally surface-treated, zirconium or cerium oxides, and also zinc, iron (black, yellow or red) or chromium oxides, manganese violet, ultramarine blue, chromium hydrate and ferric blue, or metal powders, such as aluminum powder or copper powder.

Mention may be made, among organic pigments, of carbon black, pigments of D & C type, and lakes, based on cochineal carmine, of barium, strontium, calcium or aluminum.

Mention may also be made of effect pigments, such as particles comprising an organic or inorganic and natural or synthetic substrate, for example glass, acrylic resins, polyester, polyurethane, polyethylene terephthalate, ceramics or aluminas, said substrate being covered or not being covered with metal substances, such as aluminum, gold, silver, platinum, copper or bronze, or with metal oxides, such as titanium dioxide, iron oxide or chromium oxide, and their mixtures.

The pearlescent pigments can be chosen from white pearlescent pigments, such as mica covered with titanium oxide or with bismuth oxychloride, colored pearlescent pigments, such as titanium oxide-coated mica covered with iron oxides, titanium oxide-coated mica covered with in particular ferric blue or chromium oxide, or titanium oxide-coated mica covered with an organic pigment of the abovementioned type, and pearlescent pigments based on bismuth oxychloride. Use may also be made of interferential pigments, in particular liquid crystal or multilayer pigments.

The term "alkyl" mentioned in the abovementioned compounds denotes in particular an alkyl group having from 1 to 30 carbon atoms, preferably having from 5 to 16 carbon atoms. Hydrophobic treated pigments are described in particular in application EP-A-1 086 683.

The water-soluble dyes are, for example, beetroot juice or methylene blue.

The synthetic or natural fat-soluble dyes are, for example, DC Red 17, DC Red 21, DC Red 27, DC Green 6, DC Yellow 11, DC Violet 2, DC Orange 5, Sudan red, carotenes ((3-carotene, lycopene), xanthophylls (capsanthin, capsorubin, lutein), palm oil, Sudan brown, quinoline yellow, annatto or curcumin.

The coloring materials, in particular the pigments treated with a hydrophobic agent, can be present in the composition in a content ranging from 0.1 to 50% by weight, with respect to the total weight of the composition, preferably ranging from 0.5 to 30% by weight and preferably ranging from 1 to 20% by weight.

Fillers:

The composition according to the invention can additionally comprise one or more fillers, in particular in a content ranging from 0.01 to 50% by weight, with respect to the total weight of the composition, preferably ranging from 0.01 to 30% by weight. The term "fillers" should be understood as meaning colorless or white and inorganic or synthetic particles of any shape which are insoluble in the medium of the composition, whatever the temperature at which the composition is manufactured. These fillers are used in particular to modify the rheology or the texture of the composition.

The fillers can be inorganic or organic and of any shape, platelet, spherical or oblong, whatever the crystallographic form (for example sheet, cubic, hexagonal, orthorhombic, and the like). Mention may be made of talc, mica, silica, kaolin, powders formed of polyamide (Nylon®) (Orgasol® from Atochem), powders formed of poly-β-alanine, powders formed of polyethylene, powders formed of tetrafluoroethylene polymers (Teflon®), lauroyl lysine, starch, boron nitride, hollow polymeric microspheres, such as those of poly(vinylidene chloride/acrylonitrile), such as Expancel® (Nobel Industrie), or of acrylic acid copolymers (Polytrap®) from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

In order to further improve the mattness and the persistence over time of the mattness obtained with the compositions according to the invention, the filler can be chosen from "sebum-absorbing" fillers. The sebum-absorbing filler can be an inorganic powder or an organic powder; it can be chosen from silica, powders formed of polyamides (Nylon®), powders formed of acrylic polymers, in particular of polymethyl methacrylate, of poly(methyl methacrylate/ethylene glycol dimethacrylate), of poly(allyl methacrylate/ethylene glycol dimethacrylate) or of ethylene glycol dimethacrylate/lauryl methacrylate copolymer, hollow polymeric microspheres formed of poly(vinylidene chloride/acrylonitrile), or silicone elastomer powders, which are obtained in particular by polymerization of organopolysiloxane having at least two hydrogen atoms each bonded to a silicon atom and of an organopolysiloxane comprising at least two groups possessing ethylenic unsaturation (in particular two vinyl groups), in the presence of a platinum catalyst.

The sebum-absorbing powder can be a powder coated with a hydrophobic treatment agent.

The hydrophobic treatment agent can be chosen from fatty acids, such as stearic acid, metal soaps, such as aluminum dimyristate or the aluminum salt of hydrogenated tallow glutamate, amino acids, N-acylated amino acids or their salts, lecithin, isopropyl titanium triisostearate, and their mixtures.

The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminum, magnesium, calcium, zirconium, zinc, sodium or potassium salts. The amino acid can, for example, be lysine, glutamic acid or alanine.

The term "alkyl" mentioned in the abovementioned compounds denotes in particular an alkyl group having from 1 to 30 carbon atoms, preferably having from 5 to 16 carbon atoms.

Mention may be made, as silica powder, of:
  the porous silica microspheres sold under the name Silica Beads SB-700 by Myoshi or "Sunsphere® H51" or "Sunsphere® H33" by Asahi Glass;
  the amorphous silica microspheres coated with polydimethylsiloxane sold under the name "SA Sunsphere® H 33" or "SA Sunsphere® H53" by Asahi Glass.

Mention may be made, as powder formed of acrylic polymers, of:
  the polymethyl methacrylate powders sold under the name Covabead® LH85 by Wackherr;
  the poly(methyl methacrylate/ethylene glycol dimethacrylate) powders sold under the name Dow Corning 5640 Microsponge® Skin Oil Adsorber by Dow Corning or Ganzpearl® GMP-0820 by Ganz Chemical;

the poly(allyl methacrylate/ethylene glycol dimethacrylate) powders sold under the name Poly-Pore® L200 or Poly-Pore® E200 by Amcol;

the ethylene glycol dimethacrylate/lauryl methacrylate copolymer powders sold under the name Polytrap® 6603 by Dow Corning.

Mention may be made, as hollow polymeric microspheres formed of poly(vinylidene chloride/acrylonitrile), of those sold under the name Expancel® by Nobel Industrie.

Mention may be made, as silicone elastomer powder, of the powders sold under the names "Trefil® Powder E-505C" and "Trefil® Powder E-506C" by Dow Corning.

The solid particles, such as pulverulent coloring materials (pigments and pearlescent agents) and fillers, can be completely or partially surface-treated with a compound of silicone nature, a compound of fluorinated nature, a compound of fluorinated/silicone nature, a fatty acid or amino acid or one of their mixtures.

According to a preferred embodiment, the compositions, in particular the compositions for making up or caring for the skin and in particular foundations, can comprise at least one solid particle completely or partially surface-treated with a compound of fluorinated nature, in particular in order to improve the persistence of the color and mattness.

The hydrophobic treatment agent can be chosen from silicones, such as methicones, dimethicones, perfluoroalkylsilanes, perfluoroalkylsilazanes, triethoxycapryloylsilane or triethoxysilylethyl polydimethylsiloxyethyl hexyl dimethicone; fatty acids such as stearic acid; metal soaps, such as aluminum dimyristate or the aluminum salt of hydrogenated tallow glutamate; perfluoroalkyl phosphates, polyhexafluoropropylene oxides, polyorganosiloxanes comprising perfluoroalkyl perfluoropolyether groups or silicone-grafted acrylic polymers (described in particular in application JP-A-05-339125, the content of which is incorporated by way of reference); amino acids; N-acylated amino acids or their salts; lecithin, isopropyl titanium triisostearate, isostearyl sebacate, and their mixtures.

The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminum, magnesium, calcium, zirconium, zinc, sodium or potassium salts. The amino acid can be, for example, lysine, glutamic acid or alanine.

The fluorinated surface-active agents can be chosen from perfluoroalkyl phosphates, perfluoropolyethers, polytetrafluoroethylenes (PTFEs) and perfluoroalkanes.

The perfluoropolyethers are described in particular in patent application EP-A-486 135 and are sold under the Fomblin trade names by Montefluos.

Perfluoroalkyl phosphates are described in particular in application JP H05-86984. The diethanolamine perfluoroalkyl phosphates sold by Asahi Glass under the reference AsahiGuard AG530 can be used.

Mention may be made, among linear perfluoroalkanes, of perfluorocycloalkanes, perfluoro(alkylcycloalkanes), perfluoropolycycloalkanes, aromatic perfluorinated hydrocarbons (perfluoroarenes) and organoperfluorinated hydrocarbon compounds comprising at least one heteroatom.

Mention may be made, among perfluoroalkanes, of the series of the linear alkanes, such as perfluorooctane, perfluorononane or perfluorodecane.

Mention may be made, among perfluorocycloalkanes and perfluoro(alkylcycloalkanes), of perfluorodecalin, sold under the name of "Flutec PP5 GMP" by Rhodia, perfluoro(methyldecalin) or perfluoro($C_3$-$C_5$ alkylcyclohexanes), such as perfluoro(butylcyclohexane).

Mention may be made, among perfluoropolycycloalkanes, of bicyclo[3.3.1]nonane derivatives, such as perfluorotrimethylbicyclo[3.3.1]nonane, adamantane derivatives, such as perfluorodimethyladamantane, and perfluorinated derivatives of hydrogenated phenanthrene, such as tetracosafluorotetradecahydrophenanthrene.

Mention may be made, among perfluoroarenes, of perfluorinated derivatives of naphthalene, such as perfluoronaphthalene and perfluoro-1-methylnaphthalene.

Mention may be made, as example of commercial references for pigments treated with a fluorinated compound, of:

Yellow iron oxide/perfluoroalkyl phosphate, sold under the reference PF 5 Yellow 601 by Daito Kasei, Red iron oxide/perfluoroalkyl phosphate, sold under the reference PF 5 Red R 516L by Daito Kasei, Black iron oxide/perfluoroalkyl phosphate, sold under the reference PF 5 Black BL 100 by Daito Kasei, Titanium dioxide/perfluoroalkyl phosphate, sold under the reference PF 5 TiO2 CR 50 by Daito Kasei, Yellow iron oxide/perfluoropolymethyl isopropyl ether, sold under the reference Iron Oxide Yellow BF-25-3 by Toshiki, DC Red 7/perfluoropolymethyl isopropyl ether, sold under the reference D&C Red 7 FHC by Cardre Inc., DC Red 6/PTFE, sold under the reference T 9506 by Warner-Jenkinson, Boron nitride/perfluoroperhydrophenanthrene, sold under the reference Boron nitride TBN12 by Saint Gobain Advanced Ceramics.

The composition can comprise fibers.

The term "fiber" should be understood as meaning an object with a length L and a diameter D such that L is greater than D, D being the diameter of the circle in which the cross section of the fiber is framed. In particular, the L/D ratio (or aspect ratio) is chosen within the range from 3.5 to 2500, preferably from 5 to 500 and better still from 5 to 150.

The fibers which can be used in the composition of the invention can be fibers of synthetic or natural and inorganic or organic origin. They can be short or long, individual or organized, for example braided, and hollow or solid. They can have any shape and can in particular be circular or polygonal (square, hexagonal or octagonal) in cross section, according to the specific application envisaged. In particular, their ends are blunted and/or polished to prevent injury.

In particular, the fibers have a length ranging from 1 µm to 10 mm, preferably from 0.1 mm to 5 mm and better still from 0.3 mm to 3 mm. Their cross section can be included within a circle with a diameter ranging from 2 nm to 500 µm, preferably ranging from 100 nm to 100 µm and better still from 1 µm to 50 µm. The weight or count of the fibers is often given in denier or decitex and represents the weight in grams per 9 km of yarn. Preferably, the fibers according to the invention have a count chosen within the range from 0.01 to 10 denier, preferably from 0.1 to 2 denier and better still from 0.3 to 0.7 denier.

Such fibers are described in particular in the French patent application filed under No. 0 450 074 and applications FR-A-2 844 710 and EP-A-1 201 221, the contents of which are incorporated by way of reference.

The fibers can be present in the composition in a content ranging from 0.1% to 30% by weight, with respect to the total weight of the composition, preferably ranging from 0.1% to 20% by weight and preferentially ranging from 0.1% to 10% by weight.

The composition according to the invention can also comprise ingredients commonly used in cosmetics, such as vitamins, thickeners, trace elements, softeners, sequestering agents, fragrances, basifying or acidifying agents, preservatives, sunscreens, surfactants, antioxidants, agents for combating hair loss, antidandruff agents, propellants, or their mixtures.

Of course, a person skilled in the art will take care to choose this or these optional additional compounds and/or their amounts so that the advantageous properties of the corresponding composition according to the invention are not, or not substantially, detrimentally affected by the envisioned addition.

According to another aspect, the invention also relates to a cosmetic combination comprising:
  i) a container delimiting at least one compartment, said container being closed by a closing element; and
  ii) a composition positioned inside said compartment, the composition being in accordance with the invention.

The container can have any appropriate form. It can in particular be in the form of a bottle, a tube, a pot, a box, a tin, a bag or a case.

The closing element can be in the form of a removable stopper, of a lid, of a seal, of a tear-off strip or of a capsule, in particular of the type comprising a body fixed to the container and a cap articulated over the body. It can also be in the form of an element providing the selective closure of the container, in particular a pump, a valve or a flap.

The container can be used in combination with an applicator, in particular in the form of a brush comprising an arrangement of hairs held by a twisted wire. Such a twisted brush is described in particular in U.S. Pat. No. 4,887,622. It can also be in the form of a comb comprising a plurality of application elements, obtained in particular from molding. Such combs are described, for example, in patent FR 2 796 529. The applicator can be in the form of a fine brush, such as described, for example, in patent FR 2 722 380. The applicator can be in the form of a pad of foam or elastomer, of a felt-tipped pen or of a spatula. The applicator can be free (powder puff or sponge) or integrally attached to a rod carried by the closing element, such as described, for example, in U.S. Pat. No. 5,492,426. The applicator can be integrally attached to the container, such as described, for example, in patent FR 2 761 959.

The product may be contained directly in the container or indirectly. By way of example, the product can be positioned on an impregnated support, particularly in the form of a wipe or of a wad, and can be positioned (singly or severally) in a tin or in a bag. Such a support incorporating the product is described, for example, in application WO 01/03538.

The closing element can be coupled to the container by screwing. Alternatively, the coupling between the closing element and the container is carried out other than by screwing, in particular via a bayonet mechanism, by snapping, clamping, welding or adhesive bonding, or by magnetic attraction. The term "snapping" is understood to mean in particular any system involving the crossing of a row or strip of material by elastic deformation of a portion, in particular of the closing element, and then by elastically returning said portion to the unstressed position after the row or strip has been crossed.

The container can be at least partially made of thermoplastic material. Mention may be made, as examples of thermoplastic materials, of polypropylene or polyethylene.

Alternatively, the container is made of non-thermoplastic material, in particular of glass or of metal (or alloy).

The container can have rigid walls or deformable walls, in particular in the form of a tube or of a tube bottle.

The container can comprise means intended to bring about or facilitate the distribution of the composition. By way of example, the container can have deformable walls, so as to bring about the departure of the composition in response to excess pressurization inside the container, which excess pressurization is brought about by the elastic (or non-elastic) crushing of the walls of the container. Alternatively, in particular when the product is in the form of a stick, the latter can be driven by a piston mechanism. Still in the case of a stick, in particular of a makeup product (lipstick, foundation, and the like), the container can comprise a mechanism, in particular a rack-and-pinion mechanism or a mechanism with a screw rod or a mechanism with a helical groove, capable of moving a stick in the direction of said opening. Such a mechanism is described, for example, in patent FR 2 806 273 or in patent FR 2 775 566. Such a mechanism for a liquid product is described in patent FR 2 727 609.

The container can be composed of a case with a bottom delimiting at least one receptacle comprising the composition and a lid, in particular articulated over the bottom, capable of at least partially covering said bottom. Such a case is described, for example, in application WO 03/018423 or in patent FR 2 791 042.

The container can be equipped with a drainer positioned in the vicinity of the opening of the container. Such a drainer makes it possible to wipe the applicator and optionally the rod to which it may be integrally attached. Such a drainer is described, for example, in patent FR 2 792 618.

The composition can be at atmospheric pressure inside the container (at ambient temperature) or pressurized, in particular using a propellant gas (aerosol). In the latter case, the container is equipped with a valve (of the type of those used for aerosols).

The contents of all the patents or patent applications mentioned above are incorporated by reference in the present patent application.

The composition of the invention can be provided in the form of a product for caring for or preferably making up, in particular in colored form, the skin, more specifically the face. It can be provided in the form of a foundation, a face powder, an eyeshadow, a concealer, a blusher, a product for making up the body or a semi-permanent tattooing product.

The composition according to the invention can be manufactured by known processes used generally in the cosmetics field.

The present invention also relates to a method, more specifically a cosmetic method, for caring for and/or in particular making up the skin and/or superficial body growths (in particular hair or nails) comprising the application of a composition according to the invention described above to the skin and/or its superficial body growths.

The aim of the following examples is to illustrate, without any limitation, the subject matter of the present invention. In the patent application, the contents, unless expressly indicated otherwise, are expressed by weight with respect to the total weight of the composition.

EXAMPLES

Example 1

Preparation of an MQT$^{Pr}$ Resin

The following resins are used:

Resin MQ=an MQ resin of formula $M_{0.43}Q_{0.57}$ and with $M_n=3230$ dissolved in xylene at 70.8% by weight of solids. The MQ resin was manufactured according to the techniques described by Daudt in U.S. Pat. No. 2,676,182.

Propyl T resin=a propyl silsesquioxane resin at 74.8% by weight in toluene. The propyl silsesquioxane resin was obtained by hydrolysis of propyltrichlorosilane.

An MQ resin, a propyl T resin, xylene and 1M KOH in water, in the proportions shown in table 1, are introduced into a three-necked flask equipped with a stirrer, with a temperature probe and Dean and Stark apparatus equipped with a condenser at the top. Xylene is preintroduced into the Dean and Stark apparatus in order to ensure that a level of solids at 50% is maintained in the reactor. The mixture in the reactor is maintained at a reflux temperature (between 100 and 140° C.) for at least 3 hours. Any water which is formed in the reaction mixture is continuously removed, if appropriate, and trapped in the form of an azeotrope in the Dean and Stark apparatus. After refluxing for 3 hours, the water is removed from the apparatus and heating is continued for an additional 30 minutes. After cooling the mixture, an excess of acetic acid is added in order to neutralize the KOH in the mixture. The mixture is subsequently filtered, in order to remove the salts formed, by passing it through a filter under pressure. A solvent exchange is carried out by heating the mixture in a rotary evaporator under vacuum. After removing the majority of the xylene, decamethylcyclopentasiloxane or isododecane is added while continuing to remove any residual aromatic solvent. The structures of the resulting siloxane resins are characterized by $^{29}$Si NMR spectroscopy and GPC and the results are summarized in table 2 below.

TABLE 1

| Example # | Ratio by weight of MQ/T$^{Pr}$ resins added | % by weight of MQ resin | % by weight of propyl T resin | % by weight of xylene | % by weight of 1M KOH | % by weight of acetic acid |
|---|---|---|---|---|---|---|
| 1-a | (85:15) | 59.4 | 10.5 | 29.1 | 0.9 | 0.2 |
| 1-b | (50:50) | 34.9 | 34.8 | 29.1 | 0.9 | 0.2 |
| 1-c | (30:70) | 20.9 | 48.8 | 29.2 | 0.9 | 0.2 |
| 1-d | (95:5) | 67.1 | 3.5 | 28.3 | 0.9 | 0.2 |
| 1-e | (100:0) | 69.3 | 0 | 28.8 | 0.9 | 0.2 |

TABLE 2

| Example # | Structure of the resin according to the NMR characterization | % by weight of OH | Mn | Mw | Mw/Mn |
|---|---|---|---|---|---|
| MQ resin | $M^{0.43}Q^{0.57}$ | | 3230 | 1516 | 4.7 |
| Propyl T resin | $T^{Pr}_{1.0}$ | 7.0 | 3470 | 11 400 | 3.3 |
| 1-a | $M_{0.374}Q_{0.529}{:}T^{Pr}_{0.097}$ | 1.4 | 5880 | 271 000 | 46.1 |
| 1-b | $M_{0.248}Q_{0.341}{:}T^{Pr}_{0.412}$ | 2.1 | 6640 | 3 860 000 | 581.3 |
| 1-c | $M_{0.162}Q_{0.217}{:}T^{Pr}_{0.621}$ | 1.5 | 7600 | 25 300 000 | 3329 |
| 1-d | $M_{0.419}Q_{0.5485}{:}T^{Pr}_{0.03}$ | 1.5 | | | |
| 1-e | MQ | 1.7 | 5200 | 28 900 | 5.6 |

Example 2

W/O Emulsion

According to a specific form of the invention, use is made of example 1-c described in example 1 above.

| | | % by weight |
|---|---|---|
| A1 | Cetyl PEG/PPG-10/1 Dimethicone (Abil EM90 from Goldschmidt) | 2.1 |
| | Polyglyceryl-4 Isostearate (Isolan GI34 ® from Evonik Goldschmidt) | 2.8 |
| | Hexyl laurate (Cetiol A from Cognis) | 2.1 |
| | Tristearin (and) Acetylated Glycol Stearate (Unitwix from United Guardian) | 1 |
| | Isododecane | 8.37 |
| | Disteardimonium Hectorite (and) Propylene Carbonate (bentone gel ISD V from Elementis) | 5 |
| | Undecane (and) Tridecane (Cetiol UT from Cognis) | 3.5 |
| | MQ/Propyl T resin 30:70, as prepared according to example 1-c described above, in isododecane | 11.38 |
| A2 | Dicaprylyl Carbonate (Cetiol CC from Cognis) | 5 |
| | CI 77492 & Disodium Stearoyl Glutamate & Aluminum Hydroxide (1) | 2 |
| | CI 77491 & Disodium Stearoyl Glutamate & Aluminum Hydroxide (2) | 0.65 |
| | CI 77499 & Disodium Stearoyl Glutamate & Aluminum Hydroxide (3) | 0.3 |
| | CI 77891 & Disodium Stearoyl Glutamate & Aluminum Hydroxide (4) | 11.05 |
| A3 | Nylon-12 | 3.75 |
| | Talc | 3.75 |

-continued

| | | % by weight |
|---|---|---|
| B1 | Demineralized water | 35.15 |
| | Preservatives | 1 |
| | Magnesium Sulfate | 1 |
| | TOTAL | 100% |

(1) 96.5% CI 77492 & 3.0% Disodium Stearoyl Glutamate & 0.5% Aluminum Hydroxide, sold under the name NAI-C33-9001-10 by Miyoshi Kasei
(2) 96.5% CI 77491 & 3.0% Disodium Stearoyl Glutamate & 0.5% Aluminum Hydroxide, sold under the name NAI-C33-8001-10 by Miyoshi Kasei
(3) 96.5% CI 77499 & 3.0% Disodium Stearoyl Glutamate & 0.5% Aluminum Hydroxide, sold under the name NAI-C33-7001-10 by Miyoshi Kasei
(4) 97% CI 77891 & 2.5% Disodium Stearoyl Glutamate & 0.5% Aluminum Hydroxide, sold under the name NAI-TAO-77891 by Miyoshi Kasei Procedure The constituents of phase A2 are weighed out. The mixture is passed through a triple roll mill. The constituents of phase A1 are subsequently weighed out into the main beaker and the latter is placed in a water bath (75-80° C.). When the mixture is homogeneous, it is cooled to ambient temperature.

A2 is incorporated in phase A1 with stirring with a Moritz stirrer at 1500 revolutions/min. The constituents of phase A3 are then successively added while retaining the same stirring.

The constituents of phase B are weighed out. Phase B is brought to boiling, until the constituents have completely dissolved. Phase B is cooled to 50° C.

Phase B is subsequently trickled into phase A1+A2+A3 while stirring with a Moritz stirrer at 3200 rev/min.

Protocol for Instrumental Measurements of the Immediate Mattness and the Persistence of the Mattness The mattness and the persistence of the mattness after application of said composition to the skin of the face can be measured using the protocol described below.

The mattness of a region of the skin, for example the face, is measured using a polarimetric camera, which is a black and white polarimetric imaging system, with which images are acquired in parallel (P) and crossed (C) polarized light.

By analyzing the image resulting from the subtraction of the two images (P-C), the shine is quantified by measuring the mean level of gray of the 5% of shiniest pixels corresponding to the regions of shine.

More specifically, the measurements are carried out on a panel of individuals who are kept in an air-conditioned (22° C.+/−2° C.) waiting room for 15 min before the beginning of the test. They remove their makeup and an image of one of their cheeks is acquired with the polarimetric camera. This image makes it possible to measure the shine at T0 before applying makeup. Approximately 100 mg of said composition as described above are then weighed out into a watch glass and are applied with the bare fingers to the half of the face on which the T0 measurement was carried out.

After a drying time of 15 min, an image of the made-up cheek is acquired with the polarimetric camera. This image makes it possible to measure the shine immediately after applying makeup (Timm). The models then return to the air-conditioned room for 3 h. Finally, an image of the made-up cheek after waiting for 3 h is acquired with the polarimetric camera. This image makes it possible to measure the shine after wearing makeup for 3 h (T3 h).

The results are expressed by calculating the difference (Timm−T0), which measures the effect of the makeup. A negative value means that the makeup reduces the shine of the skin and that it is thus mattifying.

The difference (T3 h−Timm) measuring the persistence of this effect is subsequently calculated. The value obtained should be as low as possible, which means that the mattness of the makeup does not change over time.

For the measurements carried out, it is considered that:
+slight effect or low persistence
++moderate effect or moderate persistence
+++significant effect or good persistence
++++very significant effect or very good persistence Protocol for Instrumental Measurements of the Immediate Color and the Persistence of the Color The same protocol as that described above for the mattness is used but, instead of measuring the shine, a colorimetric measurement of the skin, before and after applying makeup, is carried out by measuring the a*, b* and L* indices, namely the red and yellow indices and the brightness.

For each woman, an image of the cheeks is taken at T0 (before applying makeup), at Timm (15 minutes after applying makeup of said composition) and at T3 h (3 h after applying makeup), using a chromasphere, with a definition of 410×410 pixels.

Each image obtained with the camera is made use of in color. The color is quantified by the red and yellow indices, the brightness and the color difference (respectively a*, b*, L* and deltaE).

The deltaE, dE or ΔE is defined as a measurement of difference between two colors. The formula established in 1976 is shown below:

$$\Delta E^* = \sqrt{((L_1-L_2)^2+(a_1-a_2)^2+(b_1-b_2)^2)}, \text{ where:}$$

$L_1$, $a_1$ and $b_1$ are the coordinates in the colorimetric space of the first color to be compared and $L_2$, $a_2$ and $b_2$ those of the second.

Results color persistence measurements: (T3 h−Timm) grading ++++(very good)

mattness persistence measurements: (T3 h−Timm) grading +++(good)

Very good results in terms of persistence of the color and persistence of the mattness are obtained.

Furthermore, a sensory evaluation of said emulsion (W/O) was carried out on a panel of individuals who use foundation. After free application of said composition to the face, each individual evaluates the perception of said composition at the time of application and in terms of makeup result. Said composition is graded favorably: the softness of the material allows homogeneous distribution over all the regions; the foundation offers a mattifying result; the foundation is comfortable to wear and is completely forgotten.

Example No. 3

W/O Emulsion

A W/O emulsion is prepared according to the protocol described above and in which the volatile hydrocarbon oil is composed essentially of an undecane/tridecane mixture (Cetiol UT from Cognis).

|    |    | % by weight |
|----|----|-------------|
| A1 | Cetyl PEG/PPG-10/1 Dimethicone (Abil EM90 from Goldschmidt) | 2.1 |
|    | Polyglyceryl-4 Isostearate (Isolan GI34 ® from Evonik Goldschmidt) | 2.8 |
|    | Hexyl laurate (Cetiol A from Cognis) | 2.1 |
|    | Tristearin (and) Acetylated Glycol Stearate (Unitwix from United Guardian) | 1 |
|    | Disteardimonium Hectorite (and) Propylene Carbonate (bentone gel ISD V from Elementis) | 5 |
|    | Undecane (and) Tridecane (Cetiol UT from Cognis) | 11.87 |
|    | MQ/Propyl T resin 30:70, as prepared according to example 1-c described above, in isododecane | 11.38 |
| A2 | Dicaprylyl Carbonate (Cetiol CC from Cognis) | 5 |
|    | CI 77492 & Disodium Stearoyl Glutamate & Aluminum Hydroxide (1) | 2 |
|    | CI 77491 & Disodium Stearoyl Glutamate & Aluminum Hydroxide (2) | 0.65 |
|    | CI 77499 & Disodium Stearoyl Glutamate & Aluminum Hydroxide (3) | 0.3 |
|    | CI 77891 & Disodium Stearoyl Glutamate & Aluminum Hydroxide (4) | 11.05 |
| A3 | Nylon-12 | 3.75 |
|    | Talc | 3.75 |

-continued

| | % by weight |
|---|---|
| B1 Demineralized water | 35.15 |
| Preservatives | 1 |
| Magnesium Sulfate | 1 |
| TOTAL | 100% |

(1) 96.5% CI 77492 & 3.0% Disodium Stearoyl Glutamate & 0.5% Aluminum Hydroxide, sold under the name NAI-C33-9001-10 by Miyoshi Kasei
(2) 96.5% CI 77491 & 3.0% Disodium Stearoyl Glutamate & 0.5% Aluminum Hydroxide, sold under the name NAI-C33-8001-10 by Miyoshi Kasei
(3) 96.5% CI 77499 & 3.0% Disodium Stearoyl Glutamate & 0.5% Aluminum Hydroxide, sold under the name NAI-C33-7001-10 by Miyoshi Kasei
(4) 97% CI 77891 & 2.5% Disodium Stearoyl Glutamate & 0.5% Aluminum Hydroxide, sold under the name NAI-TAO-77891 by Miyoshi Kasei Example No. 4

Liquid Lipstick

| Example No. 4 | |
|---|---|
| MQ/Propyl T resin 30:70, as prepared according to example 1-c described above, in isododecane | 65.1 |
| Pigments | 2.5 |
| PDMS 5 cSt | 4.5 |
| Isododecane | 27.9 |

Example No. 5

Liquid Lipstick

| Example No. 5 | |
|---|---|
| MQ/Propyl T resin 30:70, as prepared according to example 1-c described above, in isododecane | 44.1 |
| Parleam | 10.0 |
| PDMS 5 cSt | 20.0 |
| Hydrophilic pyrogenic silica | 1.0 |
| Pigments | 2.5 |
| Undecane (and) Tridecane (Cetiol UT from Cognis) | 22.4 |

Procedure
1. A pigment mill base of the pigments is reduced in the oily phase by carrying out three passes of the mixture on the triple roll mill.
2. The mill base necessary for the composition, the nonvolatile SMs and the volatile SMs are weighed into a beaker.
3. The mixture is stirred with a Rayneri stirrer for 45 min.
  4. The formulation is poured into small pots which are leaktight with regard to the isododecane.

The invention claimed is:
1. A method for making up skin to provide a matt deposited layer, comprising applying to the skin a composition comprising, in a physiologically acceptable medium:
  i) at least one siloxane resin comprising the units:
    (i) $(R^1_3SiO_{1/2})_a$
    (ii) $(R^2_2SiO_{2/2})_b$
    (iii) $(R^3SiO_{3/2})_c$ and
    (iv) $(SiO_{4/2})_d$
  with
  $R^1$, $R^2$ and $R^3$ independently representing an alkyl group having from 1 to 8 carbon atoms, an aryl group, a carbinol group or an amino group,
  a being between 0.05 and 0.5,
  b being between zero and 0.3,
  c being greater than zero,
  d being between 0.05 and 0.6,
  a+b+c+d=1,
  provided that more than 40 mol % of the $R^3$ groups of the siloxane resin are propyl groups, and
  ii) at least one volatile $C_8$-$C_{16}$ hydrocarbon solvent in a content of 1 to 60% by weight, with respect to the total weight of said composition, wherein the volatile $C_8$-$C_{16}$ hydrocarbon solvent is a mixture of at least one $C_8$-$C_{16}$ isoalkane, and at least one volatile linear $C_8$-$C_{16}$ alkane,
  wherein the composition provides to the skin the matt deposited layer that has good persistence throughout a day.
2. The method according to claim 1, wherein the siloxane resin present in said composition comprises the units:
  (i) $(R^1_3SiO_{1/2})_a$
  (iii) $(R^3SiO_{3/2})_c$ and
  (iv) $(SiO_{4/2})_d$
  with
  $R^1$ and $R^3$ independently representing an alkyl group having from 1 to 8 carbon atoms,
  a being between 0.05 and 0.5,
  c being greater than zero,
  d being between 0.05 and 0.6,
  a+c+d=1,
  provided that more than 40 mol % of the $R^3$ groups of the siloxane resin are propyl groups.
3. The method according to claim 1, wherein said siloxane resin is obtained by a process comprising reacting:
  A) an MQ resin comprising at least 80 mol % of $(R^1_3SiO_{1/2})_a$ and $(SiO_{4/2})_d$ units,
    $R^1$ representing a methyl group,
    a and d being greater than zero,
    the ratio a/d being between 0.5 and 1.5; and
  B) a propyl T resin comprising at least 80 mol % of $(R^3SiO_{3/2})_c$ units,
    $R^3$ representing a propyl group,
    c being greater than zero,
  where the A/B ratio by weight is between 95:5 and 15:85.
4. The method according to claim 1, wherein said composition is an emulsion or an anhydrous composition.
5. The method according to claim 1, wherein said composition comprises an amount of siloxane resin, as dry matter active material, ranging from 0.5 to 60% by weight, with respect to the weight of the composition.
6. The method according to claim 1, wherein the volatile $C_8$-$C_{16}$ isoalkane solvent is isododecane, isodecane, isohexadecane, isohexyl neopentanoate or mixtures thereof.
7. The method according to claim 1, wherein the volatile linear $C_8$-$C_{16}$ hydrocarbon solvent is n-nonane, n-undecane, n-dodecane, n-tridecane, or mixtures thereof.
8. The method according to claim 1, wherein the ratio by weight of volatile $C_8$ to $C_{16}$ hydrocarbon solvent to the siloxane resin is less than 10.
9. The method according to claim 1, wherein the composition additionally comprises a compound chosen from a pasty compound, a hard or soft wax, a rheological additive, a coloring material, a polymer, or mixtures thereof.
10. The method according to claim 1, wherein said composition is a direct or inverse emulsion.

11. The method according to claim 1, wherein the composition additionally comprises a pigment or a filler not surface-treated with a hydrophobic agent, or mixtures thereof.

12. The method according to claim 1, wherein the composition additionally comprises a polymer comprising saccharide or a carboxylate group, or mixtures thereof.

13. The method of claim 2, wherein $R^1$ is a methyl group and $R^3$ is a propyl group.

14. The method according to claim 1, wherein the at least one volatile $C_8$-$C_{16}$ hydrocarbon solvent is present in an amount of 2 to 20% by weight, with respect to the total weight of the composition.

* * * * *